(12) United States Patent
Budiman et al.

(10) Patent No.: US 12,274,549 B2
(45) Date of Patent: *Apr. 15, 2025

(54) OPTIMIZING ANALYTE SENSOR CALIBRATION

(71) Applicant: ABBOTT DIABETES CARE INC., Alameda, CA (US)

(72) Inventors: Erwin Satrya Budiman, Fremont, CA (US); Wesley Scott Harper, Alameda, CA (US); Timothy Christian Dunn, San Francisco, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/977,545

(22) Filed: Oct. 31, 2022

(65) Prior Publication Data

US 2023/0051983 A1 Feb. 16, 2023

Related U.S. Application Data

(63) Continuation of application No. 17/834,004, filed on Jun. 7, 2022, now Pat. No. 11,484,234, which is a continuation of application No. 17/556,894, filed on Dec. 20, 2021, now Pat. No. 11,464,434, which is a continuation of application No. 17/328,768, filed on
(Continued)

(51) Int. Cl.
*A61B 5/1495* (2006.01)
*A61B 5/00* (2006.01)
*A61B 5/145* (2006.01)

(52) U.S. Cl.
CPC ........ *A61B 5/1495* (2013.01); *A61B 5/14532* (2013.01); *A61B 5/7221* (2013.01)

(58) Field of Classification Search
None
See application file for complete search history.

(56) References Cited

U.S. PATENT DOCUMENTS

| | | | |
|---|---|---|---|
| 3,581,062 | A | 5/1971 | Aston |
| 3,926,760 | A | 12/1975 | Allen et al. |

(Continued)

FOREIGN PATENT DOCUMENTS

| | | |
|---|---|---|
| DE | 4401400 | 7/1995 |
| EP | 0098592 | 1/1984 |

(Continued)

OTHER PUBLICATIONS

U.S. Appl. No. 12/242,823 (U.S. Pat. No. 8,219,173), filed Sep. 30, 2008 (Jul. 10, 2012).

(Continued)

*Primary Examiner* — Jay B Shah
(74) *Attorney, Agent, or Firm* — Baker Botts L.L.P.

(57) ABSTRACT

Method and apparatus for optimizing analyte sensor calibration including receiving a current blood glucose measurement, retrieving a time information for an upcoming scheduled calibration event for calibrating an analyte sensor, determining temporal proximity between the current blood glucose measurement and the retrieved time information for the upcoming calibration event, initiating a calibration routine to calibrate the analyte sensor when the determined temporal proximity is within a predetermined time period, and overriding the upcoming scheduled calibration event using the current blood glucose measurement are provided.

22 Claims, 4 Drawing Sheets

Related U.S. Application Data

May 24, 2021, now Pat. No. 11,202,592, which is a continuation of application No. 17/097,022, filed on Nov. 13, 2020, now Pat. No. 11,013,439, which is a continuation of application No. 15/604,648, filed on May 24, 2017, now abandoned, which is a continuation of application No. 14/285,575, filed on May 22, 2014, now Pat. No. 9,662,056, which is a continuation of application No. 13/544,934, filed on Jul. 9, 2012, now Pat. No. 8,744,547, which is a continuation of application No. 12/242,823, filed on Sep. 30, 2008, now Pat. No. 8,219,173.

(56)  References Cited

U.S. PATENT DOCUMENTS

| | | |
|---|---|---|
| 3,949,388 A | 4/1976 | Fuller |
| 3,960,497 A | 6/1976 | Acord et al. |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,650,547 A | 3/1987 | Gough |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,750,496 A | 6/1988 | Reinhart et al. |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,034,112 A | 7/1991 | Murase et al. |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,089,112 A | 2/1992 | Skotheim et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,145,381 A | 9/1992 | Volz |
| 5,148,812 A | 9/1992 | Verri et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,204,264 A | 4/1993 | Kaminer et al. |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,352,351 A | 10/1994 | White et al. |
| 5,354,449 A | 10/1994 | Band et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,532,686 A | 7/1996 | Urbas et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Carter et al. |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,695,623 A | 12/1997 | Michel et al. |
| 5,707,502 A | 1/1998 | McCaffrey et al. |
| 5,711,001 A | 1/1998 | Bussan et al. |
| 5,711,861 A | 1/1998 | Ward et al. |
| 5,720,295 A | 2/1998 | Greenhut et al. |
| 5,724,030 A | 3/1998 | Urbas et al. |
| 5,733,259 A | 3/1998 | Valcke et al. |
| 5,735,285 A | 4/1998 | Albert et al. |

(56) References Cited

U.S. PATENT DOCUMENTS

| | | |
|---|---|---|
| 5,741,211 A | 4/1998 | Renirie et al. |
| 5,749,907 A | 5/1998 | Mann |
| 5,772,586 A | 6/1998 | Heinonen et al. |
| 5,785,660 A | 7/1998 | van Lake et al. |
| 5,786,439 A | 7/1998 | Van Antwerp et al. |
| 5,791,344 A | 8/1998 | Schulman et al. |
| 5,792,065 A | 8/1998 | Xue et al. |
| 5,804,047 A | 9/1998 | Karube et al. |
| 5,820,551 A | 10/1998 | Hill et al. |
| 5,822,715 A | 10/1998 | Worthington et al. |
| 5,863,400 A | 1/1999 | Drummond et al. |
| 5,891,047 A | 4/1999 | Lander et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,622 A | 9/2000 | Minoz |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,130,623 A | 10/2000 | MacLellan et al. |
| 6,134,461 A | 10/2000 | Say et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,168,957 B1 | 1/2001 | Matzinger et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,212,417 B1 | 4/2001 | Ikeda et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,233,486 B1 | 5/2001 | Ekwall et al. |
| 6,237,394 B1 | 5/2001 | Harris et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,368,141 B1 | 4/2002 | VanAntwerp et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,475,372 B1 | 11/2002 | Ohara et al. |
| 6,475,750 B1 | 11/2002 | Han et al. |
| 6,478,736 B1 | 11/2002 | Mault |
| 6,484,046 B1 | 11/2002 | Say et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,522,903 B1 | 2/2003 | Berman et al. |
| 6,540,891 B1 | 4/2003 | Stewart et al. |
| 6,544,212 B2 | 4/2003 | Galley et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,587,704 B1 | 7/2003 | Fine et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |

(56) References Cited

U.S. PATENT DOCUMENTS

| | | |
|---|---|---|
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,200 B1 | 5/2004 | Stewart et al. |
| 6,731,976 B2 | 5/2004 | Penn et al. |
| 6,731,985 B2 | 5/2004 | Poore et al. |
| 6,733,446 B2 | 5/2004 | Lebel et al. |
| 6,735,183 B2 | 5/2004 | O'Toole et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,835,553 B2 | 12/2004 | Han et al. |
| 6,850,790 B2 | 2/2005 | Berner et al. |
| 6,850,859 B1 | 2/2005 | Schuh |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,010,345 B2 | 3/2006 | Hill et al. |
| 7,011,630 B2 | 3/2006 | Desai et al. |
| 7,016,713 B2 | 3/2006 | Gardner et al. |
| 7,016,720 B2 | 3/2006 | Kroll |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,052,472 B1 | 5/2006 | Miller et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,220,387 B2 | 5/2007 | Flaherty et al. |
| 7,225,535 B2 | 6/2007 | Feldman et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |

(56) References Cited

U.S. PATENT DOCUMENTS

| | | |
|---|---|---|
| 7,402,153 B2 | 7/2008 | Steil et al. |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,491,303 B2 | 2/2009 | Sakata et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,524,287 B2 | 4/2009 | Bharmi |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,577,469 B1 | 8/2009 | Aronowitz et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,620,438 B2 | 11/2009 | He |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbies et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,493 B2 | 5/2010 | Bartkowiak et al. |
| 7,736,310 B2 | 6/2010 | Taub et al. |
| 7,741,734 B2 | 6/2010 | Joannopoulos et al. |
| 7,751,864 B2 | 7/2010 | Buck, Jr. |
| 7,766,829 B2 | 8/2010 | Sloan et al. |
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,826,981 B2 | 11/2010 | Goode et al. |
| 7,831,310 B2 | 11/2010 | Lebel et al. |
| 7,842,174 B2 | 11/2010 | Zhou et al. |
| 7,857,760 B2 | 12/2010 | Brister et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,920,906 B2 | 4/2011 | Goode et al. |
| 7,938,797 B2 | 5/2011 | Estes |
| 7,946,984 B2 | 5/2011 | Brister et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 8,060,173 B2 | 11/2011 | Goode, Jr. et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,116,837 B2 | 2/2012 | Huang |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,170,803 B2 | 5/2012 | Kamath et al. |
| 8,179,266 B2 | 5/2012 | Hermle |
| 8,211,016 B2 | 7/2012 | Budiman |
| 8,216,137 B2 | 7/2012 | Budiman |
| 8,216,138 B1 | 7/2012 | McGarraugh et al. |
| 8,239,166 B2 | 8/2012 | Hayter et al. |
| 8,255,026 B1 | 8/2012 | Al-Ali |
| 8,282,549 B2 | 10/2012 | Brauker et al. |
| 8,376,945 B2 | 2/2013 | Hayter et al. |
| 8,396,670 B2 | 3/2013 | St-Pierre |
| 8,444,560 B2 | 5/2013 | Hayter et al. |
| 8,457,703 B2 | 6/2013 | Al-Ali |
| 8,484,005 B2 | 7/2013 | Hayter et al. |
| 8,532,935 B2 | 9/2013 | Budiman |
| 8,543,354 B2 | 9/2013 | Luo et al. |
| 8,571,808 B2 | 10/2013 | Hayter |
| 8,608,923 B2 | 12/2013 | Zhou et al. |
| 8,612,163 B2 | 12/2013 | Hayter et al. |
| 8,657,746 B2 | 2/2014 | Roy |
| 8,682,615 B2 | 3/2014 | Hayter et al. |
| 9,060,719 B2 | 6/2015 | Hayter et al. |
| 9,113,828 B2 | 8/2015 | Budiman |
| 9,241,631 B2 | 1/2016 | Valdes et al. |
| 9,398,872 B2 | 7/2016 | Hayter et al. |
| 9,408,566 B2 | 8/2016 | Hayter et al. |
| 9,483,608 B2 | 11/2016 | Hayter et al. |
| 9,504,471 B2 | 11/2016 | Lee et al. |
| 9,558,325 B2 | 1/2017 | Hayter et al. |
| 9,808,574 B2 | 11/2017 | Yodfat et al. |
| 10,820,842 B2 | 11/2020 | Harper |
| 10,827,954 B2 | 11/2020 | Hoss et al. |
| 10,874,338 B2 | 12/2020 | Stafford |
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 11,000,213 B2 | 5/2021 | Kamath et al. |
| 11,000,216 B2 | 5/2021 | Curry et al. |

(56) References Cited

U.S. PATENT DOCUMENTS

| | | |
|---|---|---|
| 11,013,440 B2 | 5/2021 | Lee et al. |
| 11,020,031 B1 | 6/2021 | Simpson et al. |
| 11,064,917 B2 | 7/2021 | Simpson et al. |
| 11,141,084 B2 | 10/2021 | Funderburk et al. |
| 2001/0041831 A1 | 11/2001 | Starkweather et al. |
| 2002/0010390 A1 | 1/2002 | Guice et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0043651 A1 | 4/2002 | Darrow et al. |
| 2002/0065454 A1 | 5/2002 | Lebel et al. |
| 2002/0068860 A1 | 6/2002 | Clark |
| 2002/0072784 A1 | 6/2002 | Sheppard et al. |
| 2002/0103499 A1 | 8/2002 | Perez et al. |
| 2002/0106709 A1 | 8/2002 | Potts et al. |
| 2002/0120186 A1 | 8/2002 | Keimel |
| 2002/0128594 A1 | 9/2002 | Das et al. |
| 2002/0143266 A1 | 10/2002 | Bock |
| 2002/0143372 A1 | 10/2002 | Snell et al. |
| 2002/0156355 A1 | 10/2002 | Gough |
| 2002/0161288 A1 | 10/2002 | Shin et al. |
| 2002/0169635 A1 | 11/2002 | Shillingburg |
| 2002/0177764 A1 | 11/2002 | Sohrab |
| 2002/0193679 A1 | 12/2002 | Malave et al. |
| 2003/0003524 A1 | 1/2003 | Taniike et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0065308 A1 | 4/2003 | Lebel et al. |
| 2003/0076082 A1 | 4/2003 | Morgan et al. |
| 2003/0100821 A1 | 5/2003 | Heller et al. |
| 2003/0114903 A1 | 6/2003 | Ellingboe |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0018486 A1 | 1/2004 | Dunn et al. |
| 2004/0022438 A1 | 2/2004 | Hibbard |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0127777 A1 | 7/2004 | Ruchti et al. |
| 2004/0133164 A1 | 7/2004 | Funderburk et al. |
| 2004/0135684 A1 | 7/2004 | Steinthal et al. |
| 2004/0138588 A1 | 7/2004 | Saikiey et al. |
| 2004/0138716 A1 | 7/2004 | Kon et al. |
| 2004/0142403 A1 | 7/2004 | Hetzel et al. |
| 2004/0146909 A1 | 7/2004 | Duong et al. |
| 2004/0152622 A1 | 8/2004 | Keith et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0244151 A1 | 12/2004 | Sakata et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0037482 A1 | 2/2005 | Braig et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0059871 A1 | 3/2005 | Gough et al. |
| 2005/0069892 A1 | 3/2005 | Iyengar et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0115832 A1 | 6/2005 | Simpson et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0143636 A1 | 6/2005 | Zhang et al. |
| 2005/0151976 A1 | 7/2005 | Toma |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0215871 A1 | 9/2005 | Feldman et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |

(56) References Cited

U.S. PATENT DOCUMENTS

| | | |
|---|---|---|
| 2005/0251033 A1 | 11/2005 | Scarantino et al. |
| 2005/0277164 A1 | 12/2005 | Drucker et al. |
| 2005/0277912 A1 | 12/2005 | John |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0091006 A1 | 5/2006 | Wang et al. |
| 2006/0094944 A1 | 5/2006 | Chuang |
| 2006/0094945 A1 | 5/2006 | Barman et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbies et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0258929 A1 | 11/2006 | Goode et al. |
| 2006/0258959 A1 | 11/2006 | Sode |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2006/0293576 A1 | 12/2006 | Van Antwerp et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0038044 A1 | 2/2007 | Dobbies et al. |
| 2007/0055799 A1 | 3/2007 | Koehler et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randiov et al. |
| 2007/0179434 A1 | 8/2007 | Weinert et al. |
| 2007/0191701 A1 | 8/2007 | Feldman et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0285238 A1 | 12/2007 | Batra |
| 2007/0299321 A1 | 12/2007 | Brown |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0018433 A1 | 1/2008 | Pitt-Pladdy |
| 2008/0021666 A1 | 1/2008 | Goode et al. |
| 2008/0021972 A1 | 1/2008 | Huelskamp et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0087544 A1 | 4/2008 | Zhou et al. |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0119703 A1 | 5/2008 | Brister et al. |

(56) References Cited

U.S. PATENT DOCUMENTS

| | | |
|---|---|---|
| 2008/0119705 A1 | 5/2008 | Patel et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0278332 A1 | 11/2008 | Fennel et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbies et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054748 A1 | 2/2009 | Feldman et al. |
| 2009/0054749 A1 | 2/2009 | He |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0069649 A1 | 3/2009 | Budiman |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0102678 A1 | 4/2009 | Mazza et al. |
| 2009/0105554 A1 | 4/2009 | Stahmann et al. |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0118589 A1 | 5/2009 | Ueshima et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0157430 A1 | 6/2009 | Rule et al. |
| 2009/0163789 A1 | 6/2009 | Say et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0182517 A1 | 7/2009 | Gandhi et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |

(56) References Cited

U.S. PATENT DOCUMENTS

| | | |
|---|---|---|
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0257911 A1 | 10/2009 | Thomas et al. |
| 2009/0267765 A1 | 10/2009 | Greene et al. |
| 2009/0281407 A1 | 11/2009 | Budiman |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0064764 A1 | 3/2010 | Hayter et al. |
| 2010/0081909 A1 | 4/2010 | Budiman et al. |
| 2010/0081953 A1 | 4/2010 | Syeda-Mahmood et al. |
| 2010/0121167 A1 | 5/2010 | McGarraugh et al. |
| 2010/0141656 A1 | 6/2010 | Krieftewirth |
| 2010/0145377 A1 | 6/2010 | Lai et al. |
| 2010/0152561 A1 | 6/2010 | Goodnow et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0190435 A1 | 7/2010 | Cook et al. |
| 2010/0204557 A1 | 8/2010 | Kiaie et al. |
| 2010/0230285 A1 | 9/2010 | Hoss et al. |
| 2010/0234710 A1 | 9/2010 | Budiman et al. |
| 2010/0261987 A1 | 10/2010 | Kamath et al. |
| 2010/0274515 A1 | 10/2010 | Hoss et al. |
| 2010/0280441 A1 | 11/2010 | Willinska et al. |
| 2010/0326842 A1 | 12/2010 | Mazza et al. |
| 2011/0004276 A1 | 1/2011 | Blair et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0036714 A1 | 2/2011 | Zhou et al. |
| 2011/0040163 A1 | 2/2011 | Telson et al. |
| 2011/0060530 A1 | 3/2011 | Fennell |
| 2011/0077490 A1 | 3/2011 | Simpson et al. |
| 2011/0112696 A1 | 5/2011 | Yodfat et al. |
| 2011/0148905 A1 | 6/2011 | Simmons et al. |
| 2011/0152637 A1 | 6/2011 | Kateraas et al. |
| 2011/0184268 A1 | 7/2011 | Taub |
| 2011/0208027 A1 | 8/2011 | Wagner et al. |
| 2011/0208155 A1 | 8/2011 | Palerm et al. |
| 2011/0213225 A1 | 9/2011 | Bernstein et al. |
| 2011/0257895 A1 | 10/2011 | Brauker et al. |
| 2011/0263958 A1 | 10/2011 | Brauker et al. |
| 2011/0320130 A1 | 12/2011 | Valdes et al. |
| 2012/0010642 A1 | 1/2012 | Lee et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0186997 A1 | 7/2012 | Li et al. |
| 2012/0209099 A1 | 8/2012 | Ljuhs et al. |
| 2012/0215462 A1 | 8/2012 | Goode et al. |
| 2012/0245447 A1 | 9/2012 | Karan et al. |
| 2012/0277565 A1 | 11/2012 | Budiman |
| 2012/0283542 A1 | 11/2012 | McGarraugh |
| 2012/0318670 A1 | 12/2012 | Karinka et al. |
| 2013/0035575 A1 | 2/2013 | Mayou et al. |
| 2013/0137953 A1 | 5/2013 | Harper et al. |
| 2013/0231541 A1 | 9/2013 | Hayter et al. |
| 2013/0324823 A1 | 12/2013 | Koski et al. |
| 2014/0005499 A1 | 1/2014 | Catt et al. |
| 2014/0046160 A1 | 2/2014 | Terashima et al. |
| 2014/0088392 A1 | 3/2014 | Bernstein et al. |
| 2014/0121488 A1 | 5/2014 | Budiman |
| 2014/0221966 A1 | 8/2014 | Buckingham et al. |
| 2015/0005601 A1 | 1/2015 | Hoss et al. |
| 2015/0216456 A1 | 8/2015 | Budiman |
| 2015/0241407 A1 | 8/2015 | Ou et al. |
| 2015/0366510 A1 | 12/2015 | Budiman |
| 2016/0022221 A1 | 1/2016 | Ou et al. |
| 2016/0302701 A1 | 10/2016 | Bhavaraju et al. |
| 2017/0112531 A1 | 4/2017 | Schoonmaker et al. |
| 2019/0274598 A1 | 9/2019 | Scott et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1391728 | 2/2004 |
| EP | 1419731 | 5/2004 |
| EP | 0939602 | 9/2004 |
| EP | 1850909 | 4/2010 |
| EP | 1677668 | 7/2010 |
| EP | 1 413 879 | 1/2012 |
| EP | 3575796 | 12/2019 |
| JP | 2004 358261 | 12/2004 |
| WO | WO 1996/025089 | 8/1996 |
| WO | WO 1996/035370 | 11/1996 |
| WO | WO 1997/015227 | 5/1997 |
| WO | WO 1998/035053 | 8/1998 |
| WO | WO 1999/056613 | 11/1999 |
| WO | WO 2000/049940 | 8/2000 |
| WO | WO 2000/049941 | 8/2000 |
| WO | WO 2000/059370 | 10/2000 |
| WO | WO 2000/074753 | 12/2000 |
| WO | WO 2000/078992 | 12/2000 |
| WO | WO 2001/052935 | 7/2001 |
| WO | WO 2001/054753 | 8/2001 |
| WO | WO 2002/016905 | 2/2002 |
| WO | WO 2002/058537 | 8/2002 |
| WO | WO 2003/012422 | 2/2003 |
| WO | WO 2003/032411 | 4/2003 |
| WO | WO 2003/076893 | 9/2003 |
| WO | WO 2003/082091 | 10/2003 |
| WO | WO 2003/085372 | 10/2003 |
| WO | WO 2003/094714 | 11/2003 |
| WO | WO 2004/060455 | 7/2004 |
| WO | WO 2004/061420 | 7/2004 |
| WO | WO 2005/010756 | 2/2005 |
| WO | WO 2005/041766 | 5/2005 |
| WO | WO 2005/065542 | 7/2005 |
| WO | WO 2005/070287 | 8/2005 |
| WO | WO 2005/089103 | 9/2005 |
| WO | WO 2005/011489 | 10/2005 |

(56) References Cited

FOREIGN PATENT DOCUMENTS

| WO | WO 2006/024671 | 3/2006 |
|---|---|---|
| WO | WO 2006/026741 A1 | 3/2006 |
| WO | WO 2006/079114 | 7/2006 |
| WO | WO 2006/081336 | 8/2006 |
| WO | WO 2006/086423 | 8/2006 |
| WO | WO 2007/097754 | 8/2007 |
| WO | WO 2008/021913 | 2/2008 |
| WO | WO 2008/086541 | 7/2008 |
| WO | WO 2010/099507 | 9/2010 |
| WO | WO 2011/011643 | 1/2011 |
| WO | WO 2012/142502 | 10/2012 |

OTHER PUBLICATIONS

U.S. Appl. No. 13/544,934 (U.S. Pat. No. 8,744,547), filed Jul. 9, 2012 (Jun. 3, 2014).
U.S. Appl. No. 14/285,575 (U.S. Pat. No. 9,662,056), filed May 22, 2014 (May 30, 2017).
U.S. Appl. No. 15/604,648 (US 2017/0258379), filed May 24, 2017 (Sep. 14, 2017).
U.S. Appl. No. 17/097,022 (U.S. Pat. No. 11,013,439), filed Nov. 13, 2020 (May 25, 2021).
U.S. Appl. No. 17/328,768 (U.S. Pat. No. 11,202,592), filed May 24, 2021 (Dec. 21, 2021).
U.S. Appl. No. 17/556,894 (U.S. Pat. No. 11,464,434), filed Dec. 20, 2021 (Oct. 11, 2022).
U.S. Appl. No. 17/834,004 (U.S. Pat. No. 11,484,234), filed Jun. 7, 1011 (Nov. 1, 2022).
U.S. Appl. No. 13/544,934, dated Apr. 25, 2014 Issue Fee Payment.
U.S. Appl. No. 13/544,934, dated Mar. 4, 2014 Notice of Allowance.
U.S. Appl. No. 13/544,934, dated Jan. 22, 2014 Response to Non-Final Office Action with Terminal Disclaimer.
U.S. Appl. No. 13/544,934, dated Jan. 7, 2014 Non-Final Office Action.
U.S. Appl. No. 14/285,575, dated Apr. 24, 2017 Issue Fee Payment.
U.S. Appl. No. 14/285,575, dated Feb. 24, 2017 Notice of Allowance.
U.S. Appl. No. 14/285,575, dated Jan. 27, 2017 Notice of Allowance.
U.S. Appl. No. 14/285,575, dated Jan. 12, 2017 Terminal Disclaimer.
U.S. Appl. No. 14/285,575, dated Nov. 2, 2016 Response to Non-Final Office Action.
U.S. Appl. No. 14/285,575, dated Aug. 5, 2016 Non-Final Office Action.
U.S. Appl. No. 15/604,648, dated Feb. 22, 2021 Notice of Abandonment.
U.S. Appl. No. 15/604,648, dated Sep. 1, 2020 Applicant Initiated Interview Summary.
U.S. Appl. No. 15/604,648, dated Jul. 24, 2020 Advisory Action.
U.S. Appl. No. 15/604,648, dated Jul. 14, 2020 Response to Final Office Action.
U.S. Appl. No. 15/604,648, dated May 15, 2020 Final Office Action.
U.S. Appl. No. 15/604,648, dated Feb. 3, 2020 Response to Non-Final Office Action.
U.S. Appl. No. 15/604,648, dated Nov. 1, 2019 Non-Final Office Action.
U.S. Appl. No. 17/097,022, dated Apr. 14, 2021 Issue Fee Payment.
U.S. Appl. No. 17/097,022, dated Apr. 2, 2021 Notice of Allowance.
U.S. Appl. No. 17/097,022, dated Mar. 3, 2021 Response to Non-Final Office Action.
U.S. Appl. No. 17/097,022, dated Feb. 19, 2021 Non-Final Office Action.
U.S. Appl. No. 17/328,768, dated Nov. 12, 2021 Issue Fee Payment.
U.S. Appl. No. 17/328,768, dated Nov. 10, 2021 Notice of Allowance.
U.S. Appl. No. 17/328,768, dated Oct. 27, 2021 Terminal Disclaimer.
U.S. Appl. No. 17/328,768, dated Oct. 12, 2021 Response to Non-Final Office Action.
U.S. Appl. No. 17/328,768, dated Oct. 4, 2021 Non-Final Office Action.
U.S. Appl. No. 17/556,894, dated Sep. 2, 2022 Issue Fee Payment.
U.S. Appl. No. 17/556,894, dated Aug. 2, 2022 Notice of Allowance.
U.S. Appl. No. 17/556,894, dated Jul. 19, 2022 Request for Continued Examination (RCE).
U.S. Appl. No. 17/556,894, dated Apr. 20, 2022 Notice of Allowance.
U.S. Appl. No. 17/556,894, dated Apr. 8, 2022 Response to Non-Final Office Action with Terminal Disclaimer.
U.S. Appl. No. 17/556,894, dated Mar. 15, 2022 Non-Final Office Action.
U.S. Appl. No. 17/834,004, dated Sep. 21, 2022 Issue Fee Payment.
U.S. Appl. No. 17/834,004, dated Sep. 15, 2022 Notice of Allowance.
U.S. Appl. No. 17/834,004, dated Aug. 26, 2022 Response to Non-Final Office Action with Terminal Disclaimer.
U.S. Appl. No. 17/834,004, dated Jul. 29, 2022 Non-Final Office Action.
Armour, J. C., et al., "Application of Chronic Intravascular Blood Glucose Sensor in Dogs", Diabetes, vol. 39, 1990, pp. 1519 1526.
Arnold, M. A., et al., "Selectivity Assessment of Noninvasive Glucose Measurements Based on Analysis of Multivariate Calibration Vectors", Journal of Diabetes Science and Technology, vol. 1, No. 4, 2007, pp. 454 462.
Bennion, N., et al., "Alternate Site Glucose Testing: A Crossover Design", Diabetes Technology & Therapeutics, vol. 4, No. 1, 2002, pp. 25 33.
Blank, T. B., et al., "Clinical Results from a Non Invasive Blood Glucose Monitor", Optical Diagnostics and Sensing of Biological Fluids and Glucose and Cholesterol Monitoring IT, Proceedings of SPIE, vol. 4624, 2002, pp. 1 10.
Blendea, M. C., et al., "Heart Disease in Diabetic Patients", Current Diabetes Reports, vol. 3, 2003, pp. 223 229.
Boyne, M. S., et al., "Timing of Changes in Interstitial and Venous Blood Glucose Measured with a Continuous Subcutaneous Glucose Sensor", Diabetes, vol. 52, Nov. 2003, pp. 2790 2794.
Bremer, T. M., et al., "Benchmark Data from the Literature for Evaluation of New Glucose Sensing Technologies", Diabetes Technology & Therapeutics, vol. 3, No. 3, 2001, pp. 409 418.
Brooks, S. L., et al., "Development of an On-Line Glucose Sensor for Fermentation Monitoring", Biosensors, vol. 3, 1987/88, pp. 45 56.
Cass, A. E., et al., "Ferrocene Medicated Enzyme Electrode for Amperometric Determination of Glucose", Analytical Chemistry, vol. 56, No. 4, 1984, 667 671.
Chen et al., "Glucose microbiosensor based on alumina sol gel matrix, electropolymerized composite membrane," Biosensors and Bioelectronics, 17, 1005-1013 (2002).
Chen et al., "In vivo Glucose Monitoring with Miniature "Wired" Glucose Oxidase Electrodes," Analytical Sciences, i297-i300 (2001).
Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607 613.
Choleau, C., et al., "Calibration of a Subcutaneous Amperometric Glucose Sensor Implanted for 7 Days in Diabetic Patients Part 2. Superiority of the One Point Calibration Method", Biosensors and Bioelectronics, vol. 17, No. 8, 2002, pp. 647 654.
Chung, "In vitro Evaluation of the Continuous Monitoring Glucose Sensors with Perfluorinated Tetrafluoroethylene Coatings," Bull. Korean Chem. Soc., 24(4), 514-516 (2003).
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240 1244.
Cunningham et al., "In Vivo Glucose Sensing," John Wiley & Sons, Inc. (2010).
Diabetes Control and Complications Trial Research Group, "The Effect of Intensive Treatment of Diabetes on the Development and

(56) References Cited

OTHER PUBLICATIONS

Progression of Long Term Complications in Insulin Dependent Diabetes Mellitus," New England J. Med. Vol 329, 1993, pp. 977 986.
Eckert, B. et al. "Hypoglycaemia Leads to an Increased QT Interval in Normal Men," Clinical Physiology, vol. 18, No. 6, 1998, pp. 570 575.
Eren Oruklu, M., et al., "Estimation of Future Glucose Concentrations with Subject Specific Recursive Linear Models", Diabetes Technology & Therapeutics vol. 11(4), 2009, pp. 243 253.
European Patent Application No. 09818388.2, Examination Report dated Feb. 8, 2017.
European Patent Application No. 09818388.2, Extended European Search Report dated Oct. 1, 2014.
Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
FreeStyle Navigator, Continuous Glucose Monitoring System, Abbott (2008).
Georgescu, B., et al., "Real Time Multimodel Tracking of Myocardium in Echocardiography Using Robust Information Fusion", Medical Image Computing and Computer Assisted Intervention, 2004, pp. 777 785.
Goldman, J. M., et al., "Masimo Signal Extraction Pulse Oximetly", Journal of Clinical Monitoring and Computing, vol. 16, No. 7, 2000, pp. 475-483.
Guardian Real-Time Continuous Glucose Monitoring System User Guide, Medtronic MiniMed, Inc. (2006).
Guardian® RT Continuous Glucose Monitoring System REF MMT-7900 User Guide, Medtronic MiniMed. (2005).
Guerci, B., et al., "Clinical Performance of CGMS in Type 1 Diabetic Patients Treated by Continuous Subcutaneous Insulin Infusion Using Insulin Analogs", Diabetes Care, vol. 26, 2003, pp. 582 589.
Harris, N.D., et al., "Can Changes in QT Interval be Used to Predict the Onset of Hypoglycemia in Type 1 Diabetes?", Computers in Cardiology, vol. 27, 2000, pp. 375 378.
Heise et al., "Hypoglycemia Warning Signal and Glucose Sensors: Requirements and Concepts," Diabetes Technology & Therapeutics, 5,4, 563-571 (2003).
Heller et al., "Electrochemical Glucose Sensors and Their Applications in Diabetes Management," Chem. Rev., 108, 1371-14/4, 2482-2505 (2008).
Heller, "Implanted Electrochemical Glucose Sensors for the Management of Diabetes," Annu. Rev. Biomed. Eng., 153-175 (1999).
Heller, S. R., "Abnormalities of the Electrocardiogram During Hypoglycemia: The Cause of the Dead in Bed Syndrome?" International Journal of Clinical Practice, Suppl. No. 129, 2002, pp. 27 32.
Hovorka, R., et al., "Nonlinear Model Predictive Control of Glucose Concentration in Subjects with Type 1 Diabetes", Physiological Measurement, vol. 55, Jul. 2004, pp. 905 920.
Isermann, R., "Supervision, Fault Detection and Fault Diagnosis Methods—An Introduction", Control Engineering Practice, vol. 5, No. 5, 1997, pp. 639 652.
Isermann, R., et al., "Trends in the Application of Model Based Fault Detection and Diagnosis of Technical Processes", Control Engineering Practice, vol. 5, No. 5, 1997, pp. 709 719.
Jiménez et al., "Glucose sensor based on an amperometric microelectrode with a photopolymerizable enzyme membrane," Sensors and Actuators, B 26-27, 421-424 (1995).
Johnson, P. C., "Peripheral Circulation", John Wiley & Sons, 1978, pp. 198.
Jones, T. W., et al., "Mild Hypoglycemia and Impairment of Brain Stem and Cortical Evoked Potentials in Healthy Subjects," Diabetes vol. 39, 1990, 1550 1555.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303 1304.
Kaplan, S. M., "Wiley Electrical and Electronics Engineering Dictionary", IEEE Press, 2004, pp. 141, 142, 548, 549.
Kovatchev, B. P., et al., "Evaluating the Accuracy of Continuous Glucose Monitoring Sensors", Diabetes Care, vol. 27, No. 8, 2004, pp. 1922 1928.
Kovatchev, B. P., et al., "Graphical and Numerical Evaluation of Continuous Glucose Sensing Time Lag", Diabetes Technology & Therapeutics, vol. 11, No. 3, Feb. 2009, pp. 139 143.
Kuure Kinsey, M., et al., "A Dual Rate Kalman Filter for Continuous Glucose Monitoring", Proceedings of the 28th IEEE, EMBS Annual International Conference, New York City, 2006, pp. 63 66.
Landstedt-Hallin, L., et al., "Increased QT Dispersion During Hypoglycaemia in Patients with Type 2 Diabetes Mellitus," Journal of Internal Medicine, vol. 246, 1999, 299 307.
Lodwig, V., et al., "Continuous Glucose Monitoring with Glucose Sensors: Calibration and Assessment Criteria", Diabetes Technology & Therapeutics, vol. 5, No. 4, 2003, pp. 573 587.
Lortz, J., et al., "What is Bluetooth? We Explain the Newest Short Range Connectivity Technology", Smart Computing Learning Series, Wireless Computing, vol. 8, Issue 5, 2002, pp. 72 74.
Maher, "A Method for Extrapolation of Missing Digital Audio Data", Preprints of Papers Presented at the AES Convention, 1993, pp. 1 19.
Maher, "Audio Enhancement using Nonlinear Time Frequency Filtering", AES $26^{th}$ International Conference, 2005, pp. 1 9.
Malin, S. F., et al., "Noninvasive Prediction of Glucose by Near Infrared Diffuse Reflectance Spectoscopy", Clinical Chemistry, vol. 45, No. 9, 1999, pp. 1651 1658.
Malmberg, K., "Prospective Randomised Study of Intensive Insulin Treatment on Long Term Survival After Acute Myocardial Infarction in Patients with Diabetes Mellitus", British Medical Journal, vol. 314, 1997, pp. 1512 1515.
Markel, A. et al., "Hypoglycaemia Induced Ischaemic ECG Changes", Presse Medicale, vol. 23, No. 2, 1994, pp. 78 79.
McGarraugh, G., et al., "Glucose Measurements Using Blood Extracted from the Forearm and the Finger", TheraSense, Inc., 2001, 16 Pages.
McGarraugh, G., et al., "Physiological Influences on off Finger Glucose Testing", Diabetes Technology & Therapeutics, vol. 3, No. 3, 2001, pp. 367 376.
McKean, B. D., et al., "A Telemetry Instrumentation System for Chronically Implanted Glucose and Oxygen Sensors", IEEE Transactions on Biomedical Engineering, vol. 35, No. 7, 1988, pp. 526 532.
Moatti-Sirat et al., "Evaluating in vitro and in vivo the interference of ascorbate and acetaminophen on glucose detection by a needle-type glucose sensor," Biosensors & Bioelectronics 7, 345-352 (1992).
Morbiducci, U, et al., "Improved Usability of the Minimal Model of Insulin Sensitivity Based on an Automated Approach and Genetic Algorithms for Parameter Estimation", Clinical Science, vol. 112 2007, pp. 257 263.
Mougiakakou, et al., "A Real Time Simulation Model of Glucose Insulin Metabolism for Type 1 Diabetes Patients", Proceedings of the 2005 IEEE, 2005, pp. 298 301.
Nishida et al., "Development of a ferrocene-mediated needle-type glucose sensor covered with newly designed biocompatible membrane, 2-methacryloyloxyethyl phosphorylcholine-co-n-butyl methacrylate," Medical Progress through Technology, 21, 91-123 (1995).
Okin, P. M., et al., "Electrocardiographic Repolarization Complexity and Abnormality Predict All Cause and Cardiovascular Mortality in Diabetes," Diabetes, vol. 53, 2004, pp. 434 440.

(56) References Cited

OTHER PUBLICATIONS

Panteleon, A. E., et al., "The Role of the Independent Variable to Glucose Sensor Calibration", Diabetes Technology & Therapeutics, vol. 5, No. 3, 2003, pp. 401 410.
Parker, R., et al., "Robust Hoe Glucose Control in Diabetes Using a Physiological Model", AIChE Journal, vol. 46, No. 12, 2000, pp. 2537 2549.
PCT Application No. PCT/US2009/058895, International Preliminary Report on Patentability dated Apr. 14, 2011.
PCT Application No. PCT/US2009/058895, International Search Report and Written Opinion of The International Searching Authority dated Nov. 20, 2009.
Peterson, K., et al., Regulation of Serum Potassium During Insulin Induced Hypoglycemia, Diabetes, vol. 31, 1982, pp. 615 617.
Pickup, J., et al., "Implantable Glucose Sensors: Choosing the Appropriate Sensing Strategy", Biosensors, vol. 3, 1987/88, pp. 335 346.
Pickup, J., et al., "In Vivo Molecular Sensing in Diabetes Mellitus: An Implantable Glucose Sensor with Direct Electron Transfer", Diabetologia, vol. 32, 1989, pp. 213 217.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268 2272.
Quinn, C. P., et al., "Kinetics of Glucose Delivery to Subcutaneous Tissue in Rats Measured with 0.3 mm Amperometric Microsensors", The American Physiological Society, 1995, E155 E161.
Rana, B. S., et al., "Relation of QT Interval Dispersion to the Number of Different Cardiac Abnormalities in Diabetes Mellitus", The American Journal of Cardiology, vol. 90, 2002, pp. 483 487.
Rhodes et al., "Prediction of Pocket-Portable and Implantable Glucose Enzyme Electrode Performance from Combined Species Permeability and Digital Simulation Analysis," Anal. Chem., 66, 1520-1529 (1994).
Robinson, R. T. C. E., et al. "Changes in Cardiac Repolarization During Clinical Episodes of Nocturnal Hypoglycaemia in Adults with Type 1 Diabetes," Diabetologia, vol. 47, 2004, pp. 312 315.
Roe, J. N., et al., "Bloodless Glucose Measurements", Critical Review in Therapeutic Drug Carrier Systems, vol. 15, Issue 3, 1998, pp. 199 241.
Sakakida, M., et al., "Development of Ferrocene Mediated Needle Type Glucose Sensor as a Measure of True Subcutaneous Tissue Glucose Concentrations", Artificial Organs Today, vol. 2, No. 2, 1992, pp. 145 158.
Sakakida, M., et al., "Ferrocene Mediated Needle Type Glucose Sensor Covered with Newly Designed Biocompatible Membrane", Sensors and Actuators B, vol. 13 14, 1993, pp. 319 322.
Salehi, C., et al., "A Telemetry Instrumentation System for Long Term Implantable Glucose and Oxygen Sensors", Analytical Letters, vol. 29, No. 13, 1996, pp. 2289 2308.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294 299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401 406.
Shichiri, M., et al., "Glycaemic Control in Pancreatectomized Dogs with a Wearable Artificial Endocrine Pancreas", Diabetologia, vol. 24, 1983, pp. 179 184.
Shichiri, M., et al., "In Vivo Characteristics of Needle Type Glucose Sensor Measurements of Subcutaneous Glucose Concentrations in Human Volunteers", Hormone and Metabolic Research Supplement Series, vol. 20, 1988, pp. 17 20.
Shichiri, M., et al., "Membrane Design for Extending the Long Life of an Implantable Glucose Sensor", Diabetes Nutrition and Metabolism, vol. 2, 1989, pp. 309 313.
Shichiri, M., et al., "Needle type Glucose Sensor for Wearable Artificial Endocrine Pancreas", Implantable Sensors for Closed Loop Prosthetic Systems, Chapter 15, 1985, pp. 197 210.
Shichiri, M., et al., "Telemetry Glucose Monitoring Device with Needle Type Glucose Sensor: A Useful Tool for Blood Glucose Monitoring in Diabetic Individuals", Diabetes Care, vol. 9, No. 3, 1986, pp. 298 301.
Shichiri, M., et al., "Wearable Artificial Endocrine Pancreas with Needle Type Glucose Sensor", The Lancet, 1982, pp. 1129 1131.
Shults, M. C., et al., "A Telemetry Instrumentation System for Monitoring Multiple Subcutaneously Implanted Glucose Sensors", IEEE Transactions on Biomedical Engineering, vol. 41, No. 10, 1994, pp. 937 942.
Steil, G. M., et al., "Closed Loop Insulin Delivery the Path of Physiological Glucose Control", Advanced Drug Delivery Reviews, vol. 56, 2004, pp. 125 144.
Steil, G. M., et al., "Determination of Plasma Glucose During Rapid Glucose Excursions with a Subcutaneous Glucose Sensor", Diabetes Technology & Therapeutics, vol. 5, No. 1, 2003, pp. 27 31.
Steinhaus, B. M., et al., "The Information Content of the Cardiac Electrogram at the Stimulus Site," Annual International Conference of the IEEE Engineering in Medicine and Biology Society, vol. 12, No. 2, 1990, 0607 0609.
Sternberg, R., et al., "Study and Development of Multilayer Needle Type Enzyme Based Glucose Microsensors", Biosensors, vol. 4, 1988, pp. 27 40.
Summary of Safety and Effectiveness Data, Abbott Diabetes Care, 27 pages (2008).
Thompson, M., et al., "In Vivo Probes: Problems and Perspectives", Clinical Biochemistry, vol. 19, 1986, pp. 255 261.
Turner, A., et al., "Diabetes Mellitus: Biosensors for Research and Management", Biosensors, vol. 1, 1985, pp. 85 115.
U.S. Appl. No. 12/242,823, Notice of Allowance dated Apr. 27, 2012.
U.S. Appl. No. 12/242,823, Office Action dated Apr. 6, 2012.
U.S. Appl. No. 12/242,823, Office Action dated Nov. 23, 2011.
U.S. Appl. No. 13/544,934, Notice of Allowance dated Mar. 4, 2014.
U.S. Appl. No. 13/544,934, Office Action dated Jan. 7, 2014.
U.S. Appl. No. 14/077,004, Office Action dated Jul. 26, 2016.
U.S. Appl. No. 14/285,575, Notice of Allowance dated Jan. 27, 2017.
U.S. Appl. No. 14/285,575, Office Action dated Aug. 5, 2016.
U.S. Appl. No. 15/334,274, Office Action dated Apr. 25, 2019.
Updike, S. J., et al., "Principles of Long Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117 137.
Velho, G., et al., "Strategies for Calibrating a Subcutaneous Glucose Sensor", Biomedica Biochimica Acta, vol. 48, 1989, pp. 957-964.
Whipple, G., "Low Residual Noise Speech Enhancement Utilizing Time Frequency", Proceedings of the International Conference on Acoustics, Speech, and Signal Processing, vol. 19, 1994, pp. I/5-I/8.
Wilson, G. S., et al., "Progress Toward the Development of an Implantable Sensor for Glucose", Clinical Chemistry, vol. 38, No. 9, 1992, pp. 1613 1617.
Wolfe, P. J., et al., "Interpolation of Missing Data Values for Audio Signal Restoration Using a Gabor Regression Model", 2005 IEEE International Conference on Acoustics, Speech, and Signal Processing, vol. 5, 2005, pp. 517 520.
Yang et al., "Glucose Biosensors Based on Oxygen Electrode with Sandwich-Type Membranes," Annals of Biomedical Engineering, 23, 833-839 (1995).
Yang et al., "Glucose Biosensors with Enzyme Entrapped in Polymer Coating," Biomedical Instrumentation & Technology, 29(2):125-133 (1995).
U.S. Appl. No. 61/227,967, filed Jul. 23, 2009, Hoss, et al.
"In Vivo Glucose Sensing", Chemical Analysis, A Series of Monographs on Analytical Chemistry and its Applications, vol. 174, 466 pages (2010).
Abel, et al., "Biosensors for in vivo glucose measurement: can we cross the experimental stage", Biosensors and Bioelectronics, 17:1059-1070 (2002).

(56) References Cited

OTHER PUBLICATIONS

Alcock, et al., "Continuous Analyte Monitoring to Aid Clinical Practice", IEEE Engineering in Medicine and Biology, pp. 319-325 (1994).
Bard, et al., Electrochemical Methods, Fundamentals and Applications, pp. 174-175 (1980).
Bequette, "Continuous Glucose Monitoring: Real Time Algorithms for Calibration, Filtering, and Alarms", Journal of Diabetes Science and Technology, 4(2):404-418 (2010).
Cengiz, et al., "A Tale of Two Compartments: Interstitial Versus Blood Glucose Monitoring", Diabetes Technology & Therapeutics, 11(1):S-11-S16 (2009).
Chen, et al., "Defining the Period of Recovery of the Glucose Concentration after Its Local Perturbation by the Implantation of a Miniature Sensor", Clin Chem Lab Med, 40(8):786-789 (2002).
Chen, et al., "In Situ Assembled Mass-Transport Controlling Micromembranes and Their Application in Implanted Amperometric Glucose Sensors", Analytical Chemistry, 72(16):3757-3763 (2000).
Choleau, et al., "Calibration of a subcutaneous amperometric glucose sensor Part 1. Effect of measurement uncertainties on the determination of sensor sensitivity and background current", Biosensors and Bioelectronics, 17:641-646 (2002).
Csbregi, et al., "Design, Characterization, and One-Point in Vivo Calibration of a Subcutaneously Implanted Glucose Electrode", Anal. Chem., 66(19):3131-3138 (1994).
De Block, et al., "Minimally-Invasive and Non-Invasive Continuous Glucose Monitoring Systems: Indications, Advantages, Limitations and Clinical Aspects", Current Diabetes Reviews, 4:159-168 (2008).
Facchinetti, et al., "Enhanced Accuracy of Continuous Glucose Monitoring by Online Extended Kalman Filtering", Diabetes Technology & Therapeutics, 12(5):353-363 (2010).
Fischer, "Fundamentals of Glucose Sensors", Diabetic Medicine, 8:309-321 (1991).
Fraser, "An Introduction to in vivo Biosensing: Progress and Problems", Biosensors in the Body: Continuous in vivo Monitoring, pp. 1-56 (1997).
Frost, et al., "Implantable chemical sensors for real-time clinical monitoring: progress and challenges", Current Opinion in Chemical Biology, 6:63 3-641 (2002).
Gerritsen, et al., "Subcutaneously implantable glucose sensors in patients with diabetes mellitus; still many problems", Dutch Journal of Medicine, 146(28):1313-1316 (2002) (with English Machine Translation).
Heinemann, "Continuous Glucose Monitoring by Means of the Microdialysis Technique: Underlying Fundamental Aspects", Diabetes Technology & Therapeutics, 5(4):545-561 (2003).
Johnson, et al., "Reduction of Electrooxidizable Interferent Effects: Optimization of the Applied Potential for Amperometric Glucose Sensors", Electroanalysis, 6:321-326 (1994).
Knobbe, et al., "The Extended Kalman Filter for Continuous Glucose Monitoring", Diabetes Technology & Therapeutics, 7(1):15-27 (2005).
Koudelka, et al., "In-vivo Behaviour of Hypodermically Implanted Microfabricated Glucose Sensors", Biosensors & Bioelectronics, 6:31-36 (1991).
Koudelka-Hep, "Electrochemical Sensors for in vivo Glucose Sensing", Biosensors in the Body: Continuous in vivo Monitoring, pp. 57-77 (1997).
Kuure-Kinsey, et al., "A Dual-Rate Kalman Filter for Continuous Glucose Monitoring", Proceedings of the 28th IEEE, EMBS Annual International Conference, pp. 63-66 (2006).
Kvist, et al., "Recent Advances in Continuous Glucose Monitoring: Biocompatibility of Glucose Sensors for Implantation in Subcutis", Journal of Diabetes Science and Technology, 1(5):746-752 (2007).
Ming Li, et al., "Implantable Electrochemical Sensors for Biomedical and Clinical Applications: Progress, Problems, and Future Possibilities", Current Medicinal Chemistry, 14:937-951 (2007).

Onuki, et al., "A Review of the Biocompatibility of Implantable Devices: Current Challenges to Overcome Foreign Body Response", Journal of Diabetes Science and Technology, 2(6):1003-1015 (2008).
Palerm, et al., "Hypoglycemia Prediction and Detection Using Optimal Estimation", Diabetes Technology & Therapeutics, 7(1):3-14 (2005).
Poitout, et al., "Calibration in dogs of a subcutaneous miniaturized glucose sensor using a glucose meter for blood glucose determination", Biosensors & Bioelectronics, 7:587-592 (1992).
Rebrin, et al., "Subcutaneous glucose predicts plasma glucose independent of insulin: implications for continuous monitoring", American Journal of Physiology-Endocrinology and Metabolism, 277(3):E561-E571 (1999).
Renard, "Implantable glucose sensors for diabetes monitoring", Min Invas Ther & Allied Technol, 13(2):78-86 (2004).
Robert, "Continuous Monitoring of Blood Glucose", Horm Res 57(suppl 1): 81-84 (2002).
Schlosser, et al., "Biocompatibility of Active Implantable Devices", Biosensors in the Body: Continuous in vivo Monitoring, pp. 139-170 (1997).
Schmidt, et al., "Calibration of a wearable glucose sensor", The International Journal of Artificial Organs, 15(1):55-61 (1992).
Schmidtke, et al., "Accuracy of the One-Point in Vivo Calibration of "Wired" Glucose Oxidase Electrodes Implanted in Jugular Veins of Rats in Periods of Rapid Rise and Decline of the Glucose Concentration", Anal. Chem., 70:2149-2155 (1998).
Tierney, et al., "Effect of Acetaminophen on the Accuracy of Glucose Measurements Obtained with the GlucoWatch Biographer", Diabetes Technology & Therapeutics, 2(2):199-207 (2000).
Voskerician, et al., "Sensor Biocompatibility and Biofouling in Real-Time Monitoring", Wiley Encyclopedia of Biomedical Engineering, (John Wiley & Sons, Inc.), pp. 1-19 (2006).
Ward, "A Review of the Foreign-body Response to Subcutaneously-implanted Devices: The Role of Macrophages and Cytokines in Biofouling and Fibrosis", Journal of Diabetes Science and Technology, 2(5):768-777 (2008).
Ward, et al., "A new amperometric glucose microsensor: in vitro and short-term in vivo evaluation", Biosensors & Bioelectronics, 17:181-189 (2002).
Chen, et al., "A novel fault-tolerant sensor system for sensor drift compensation", Sensors and Actuators, A 147:623-632 (2008).
FreeStyle Navigator Continuous Glucose Monitoring System, Summary of Safety and Effectiveness Data in support of Pre-Market Approval (PMA) No. P050020, Abbott Diabetes Care, 7 pages (2008).
FreeStyle Navigator Continuous Glucose Monitoring System, User Guide, Abbott Diabetes Care Inc., 195 pages (2008).
Gerritsen, et al., "Performance of subcutaneously implanted glucose sensors for continuous monitoring", The Netherlands Journal of Medicine, 54:167-179 (1999).
Kalivas, et al., "Compensation for Drift and Interferences in Multicomponent Analysis", Laboratory for Chemometrics, Department of Chemistry, University of Washington, 38 pages (1982).
Thévenot, et al., "Electrochemical Biosensors: Recommended Definitions and Classification (Technical Report)", Pure Appl. Chem. 71(12):2333-2348 (1999).
U.S. Appl. No. 12/842,013 Office Action mailed Aug. 26, 2015.
U.S. Appl. No. 12/842,013 Office Action mailed Mar. 23, 2016.
U.S. Appl. No. 12/842,013 Office Action mailed Nov. 6, 2014.
Walt, et al., "The chemistry of enzyme and protein immobilization with glutaraldehyde", Trends in Analytical Chemistry, 13(10):425-430 (1994).
Zhang, "Investigations of potentially implantable glucose sensors", University of Kansas, 24 pages (1991).
Atanasov, et al., "Implantation of a refillable glucose monitoring-telemetry device", Biosensors & Bioelectronics, 12(7):669-680 (1997).
Bindra, "Developmen of potentially implantable glucose sensors", The University of Arizona, 227 pages (1990).
FreeStyle Navigator Continuous Glucose Monitoring System, User's Guide, Abbott Diabetes Care Inc., 38 pages (2008).

(56) References Cited

OTHER PUBLICATIONS

Kerner, et al., The function of a hydrogen peroxide-detecting electroenzymatic glucose electrode is markedly impaired in human sub-cutaneous tissue and plasma, Biosensors & Bioelectronics, 8:473-482 (1993).
Koschinsky, et al., "Sensors for glucose monitoring: technical and clinical aspects", Diabetes/Metabolism Research and Reviews, 17:113-123 (2001).
Koschwanez, et al., "In vitro, in vivo and post explanation testing of glucose-detecting biosensors: Current methods and recommencations", Biomaterials, 28:3687-3703 (2007).
Moussy, et al. "Performance of Subcutaneously Implanted Needle-Type Glucose Sensors Employing a Novel Trilayer Coating", Anal. Chem., 65:2072-2077 (1993).
Pickup, et al., "In vivo glucose sensing for diabetes management: progress towards non-invasive monitoring", BMJ, 319, pp. 1-4 (1999).
Pickup, et al., "Responses and calibration of amperometric glucose sensors implanted in the subcutaneous tissue of man", Acta Diabetol, 30:143-148 (1993).
Ward, et al., "Rise in background current over time in a subcutaneous glucose sensor in the rabbit: relevance to calibration and accuracy", Biosensors & Bioelectronics, 15:53-61 (2000).
Wilson, et al., "Biosensors for real-time in vivo measurements", Biosensors and Bioelectronics, 20:2388-2403 (2005).
Wisniewski, et al., "Analyte flux through chronically implanted subcutaneous polyamide membranes differs in humans and rats", Am J Physiol Endocrinol Metab, 282:E1316-E1323 (2002).
"Abbott Receives CE Mark for Freestyle™ Libre, A Revoluntionary Glucose Monitoring System for People with Diabetes," 8 pages (2023).
"FDA authorizes first fully interoperable continuous glucose monitoring system, streamlines review pathway for similar devices," FDA News Release, https://www.fda.gov/news-events/press-announcements/fda-authorizes-first-fully-interoperable-continuous-glucose-monitoring-system-streamlines-review, 3 pages, Mar. 27, 2018.
ATTD Program, 4 pages (2009).
Boise, Interview with Dexcom CEO, Dexcom CEO Kevin Sayer Explains G6, 9 pages (2018).
Cambridge Dictionary of American English, Cambridge University Press, 3 pages (2000)—Recess.
Dexcom (DXCM) Company Profile, 2017/Q4 Earnings call transcript, 12 pages (2017).
Dexcom (DXCM) Q1 2018 Results—Earnings Call Transcript, 4 pages (2018).
Dexcom G6 Continuous Glucose Monitoring System User Guide, 7 pages (2020).
DexcomG6, Continuous Glucose Monitoring System, User Guide, 22 pages (2020).
DexcomG6, Start Here, Set up, Dexcom G6 Continuous Glucose Monitoring (CGM) System (G6), 8 pages (2019).
DexcomG6, Using Your G6, 7 pages (Mar. 2020).
Email communication from Sophie Hood, Jan. 24, 2023, 6 pages.
Excerpts from Expert Report of Catharine M. Lawton—Ex. 36, Spruce Point Capital Management, Does Dexcom Really Have A Future If It Can't Match Abbott's Scale? 2 pages, Mar. 21, 2019.
Figures for U.S. Appl. No. 10,973,443 issued Apr. 13, 2021, 2 pages.
U.S. Appl. No. 60/687,199, filed Jun. 2, 2005, 12 pages.
U.S. Appl. No. 61/155,889, filed Feb. 26, 2009, 55 pages.
FreeStyle Navigator Continuous Glucose Monitoring System, Pre Market Approval Letter from the FDA, Mar. 12, 2008, 7 pages.
Funderburk et al., Joint Declaration, U.S. Appl. No. 15/963,828, 11 pages (2020).
Hall, Interview with Kevin Sayer, President and CEO of Dexcom About The New Dexcom G6, College Diabetes Network, 6 pages (2021).
Hoss et al., "Continuous Glucose Monitoring in Subcutaneous Tissue Using Factory-Calibrated Sensors: A Pilot Study," Diabetes Technology & Therapeutics, vol. 12, No. 8, pp. 591-597 (2010).
Hoss et al., "Continuous glucose monitoring in the tissue: Do we really need to calibrate in-vivo?," Diabetes Technology & Therapeutics, vol. 11, No. 2, 23 pages (2009).
Hoss et al., "Feasibility of Factory Calibration for Subcutaneous Glucose Sensors in Subjects with Diabetes," Journal of Diabetes Science and Technology, 8(1):89-94 (2014).
IEEE 10 The Authoritative Dictionary of IEEE Standards Terms, $7^{th}$ Ed., 3 pages (2020).
Merriam-Webster's Collegiate Dictionary, $10^{th}$ Ed., 4 pages (1999)—Housing and recess.
Merriam-Webster's Collegiate Dictionary, $10^{th}$ Ed., 4 pages (1999)—Release and retain.
Non-Final Office Action for U.S. Appl. No. 14/884,622 dated Jun. 13, 2018, 7 pages.
Non-Final Office Action for U.S. Appl. No. 17/030,030 dated Dec. 17, 2020, 7 pages.
Notice of Allowance for U.S. Appl. No. 15/963,828 dated Mar. 3, 2021, 32 pages.
Omnipod image, Exhibit 182, 2 pages, Sep. 22, 2022.
Response to Non-Final Office Action for U.S. Appl. No. 15/963,828, filed Dec. 8, 2020, 17 pages.
Response to Restriction Requirement for U.S. Appl. No. 14/884,622, filed Apr. 5, 2018, 15 pages.
S&P Global Market Intelligence "DexCom, Inc. NasdaqGS:DXCM, Company Conference Presentation," 17 pages (2021).
S&P Global Market Intelligence "DexCom, Inc. NasdapGS:DXCM, Company Conference Presentation,"10 pages (2020).
S&P Global Market Intelligence "DexCom, Inc. NasdaqGS:DXCM, Company Conference Presentation," 11 pages (2019).
Sayer, CGMS Changing Diabetes Management: Kevin Sayer, DIC Interview Transcript, Featuring Steve Freed, 11 pages (2019).
Sonix, Dexcom CEO—Prime Position in Our Market—Mad Money—CNBC.mp4, 4 pages (2023).
Tegnestedt et al., "Levels and sources of sound in the intensive care unit—an observational study of three room types," Acta Anaesthesiol Scand, 11 pages (2013).
The Chambers Dictionary, Chambers Harrap Publishers Ltd (1998/1999), 4 pages (2000)—Retract.
The miniMed Paradigm® REAL-Time Insulin Pump and Continuous Glucose Monitoring System, Insulin Pump User Guide, Paradigm® 522 and 722 Insulin Pumps, 25 pages (2008).
The New Oxford American Dictionary, Oxford University Press, 3 pages (2001)—Retract.
The New Penguin English Dictionary, Penguin Books, 4 pages (2000)—Recess.
U.S. Food & Drug Administration, "Deciding When to Submit a 510(k) for a Change to an Existing Device, Guidance for Industry and Food and Drug Administration Staff," 78 pages (2017).
U.S. Food & Drug Administration,"Deciding When to Submit a 510(k) for a Software Change to an Existing Device, Guidance for Industry and Food and Drug Administration Staff," 32 pages (2017).
U.S. Pat. No. 10,827,954 issued Nov. 10, 2020.
U.S. Pat. No. 10,973,443 issued Apr. 13, 2021.
Watkin,"An Introduction to Flash Glucose Monitoring," 16 pages (2013).
Webster's New College Dictionary, 2 pages (2001)—Alcove.
Webster's Third New International Dictionary, 5 pages (1993)—Retract.
Knobbe et al., Symposium Paper, "The Extended Kalman Filter for Continuous Glucosse Monitoring," Diabetes Technology & Therapeutics, 7, 1, 15-27 (2005).
Dock, E. et al., "Multivariate data analysis of dynamic amperometric biosensor responses from binary analyte mixtures—application of sensitivity correction algorithms", Talanta 65, pp. 298-305 (2005).
Hoss, U. et al., "Factory-Calibrted Continuous Glucose Sensors: The Science Behind the Technology", Diabetes Technology & Therapeutics, vol. 19, Suppl. 2, pp. S-44-S-50 (2017).
Hanson, K. et al., "Comparison of Point Accuracy Between Two Widely Used Continuous Monitoring Systems", Journal of Diabetes Science and Technology, 2024, pp. 1-10.

(56) References Cited

OTHER PUBLICATIONS

Abbott Press Release—"Abbott Receives CE Mark for FreeStyle® Libre, A Revolutionary Glucose Monitoring System for People with Diabetes" retrieved from https://abbott.mediaroom.com/2014-09-03-Abbott-Receives-CE-Mark-for-FreeStyle-Libre-a-Revolutionary-Glucose-Monitoring-System-for-People-with-Diabetes/, Sep. 3, 2014, 3 pages.

Abbott Press Release—"Abbott Receives FDA Approval for the FreeStyle Libre Pro™ System, A Revolutionary Diabetes Sensing Technology for Healthcare Professionals to Use with their Patients" retrieved from https://abbott.mediaroom.com/2016-09-28-Abbott-Receives-FDA-Approval-for-the-FreeStyle-Libre-Pro-System-a-Revolutionary-Diabetes-Sensing-Technology-for-Healthcare-Professionas-to-use-with-their-Patients/, Sep. 28, 2016, 5 pages.

Abbott Press Release—"Abbott's FreeStyle® Libre 14 Day Flash Glucose Monitoring System Now Approved in U.S." retrieved from https://abbot.mediaroom.com/2018/-07-27-Abbotts-FreeStyle-R-Libre-14-Day-Flash-Glucose-Monitoring-System-Now-Approved-in-U-S/, Jul. 27, 2018, 3 pages.

Anzhsn, National Horizon Scanning Unit Horizon Scanning Report, "GlucoWatch® G2 Biographer for the non-invasive monitoring of glucose levels", 46 pages, May 2004.

Cather, CGM Frustrations Survey dated Jun. 2020, 37 pages in *Abbott Diabetes Care Inc., et al.* v. *Dexcom, Inc.* Case No. 1:21-cv-00977-KAJ (District of Delaware).

Clinical Trials, Competitor and Ecosystem Players dated Jun. 25, 2020, 29 pages in *Abbott Diabetes Care Inc., et al.* v. *Dexcom,Inc.*, Case No. 1:21-cv-00977-KAJ (District of Delaware).

Delcaration of Dr. Anthony Edward Cass in Support of Petition for Inter Partes Review of U.S. Pat. No. 11,020,031 in *Abbott Diabetes Care Inc.* v. *Dexom, Inc.*, Case No. IPR2024-00890, In the United States Patent and Trademark Office, Before the Patent Trial and Appeal Board, May 10, 2024, 138 pages.

Declaration of Karl R. Leinsing, MSME, PE, in Support of Abbott's Motion for Summary Judgement dated May 19, 2023, 81 pages in *Abbott Diabetes Care Inc., et al.,* v. *Dexcom, Inc.,* Case No. 1:21-cv-00977-KAJ (District of Delaware).

Effectiveness and Safety Study of the DexCom™ G4 Continuous Glucose Monitoring System, DexCom, Inc., U.S. National Library of Medicine, ClinicalTrials.gov Identifier: NCT01111370, 4 pages (2017).

E-mail Communication from Christopher M. Dougherty regarding Bi Monthly Global Commercial Insights Meeting dated Dec. 17, 2019, 69 pages in *Abbott Diabetes Care inc., et al.* v. *Dexcom, Inc.,* Case No. 1:21-cv-00977-KAJ (District of Delaware).

U.S. Design U.S. Appl. No. 29/101,218, filed Feb. 25, 1999, 11 pages.

U.S. Pat. No. 11,2020,031 issued Jun. 1, 2021, 1058 pages.

FreeStyle Libre 2 HCP Pulse, Mar. 2021 Report, dated Mar. 1, 2021, 14 pages in *Abbott Diabetes Care Inc., et al.* v. *Dexcom, Inc.,* Case No. 1:21-cv-00977-KAJ (District of Delaware).

Godek, et al., Chapter 2, "The Macrophage in Wound Healing Surrounding Implanted Devices", In vivo Glucose Sensing, 36 pages (2010).

Gross, et al., "Performance Evaluation of the MiniMed® Continuous Glucose Monitoring System During Patient Home Use", Diabetes Technology & Therapeutics, vol. 2, No. 2, pp. 49-56 (2000).

Heller, "Integrated Medical Feedback Systems for Drug Delivery", American Institute of Chemical Engineers Journal, vol 51, No. 4, pp. 1054-1066 (2005).

Henning, Chapter 5, "Commercially Available Continuous Glucose Monitoring Systems", In Vivo Glucose Sensing, 50 pages (2010).

Lesperance, et al., "Calibration of the Continuous Glucose Monitoring System for Transient Glucose Monitorin", Diabetes Technology & Therapeutics, vol. 9, No. 2, pp. 183-190 (2007).

Project Status Update, Glucose Sensor Applicator Dexcom (project #2554), Design Concepts, Inc., 6 pages (2014).

Seargrove Partners, International Diabets Device, 2022 Blue Book dated 2022, 143 pages in *Abbott Diabetes Care Inc.,* v. *Dexcom, Inc.,* Case No. 1:21-cv-00977-KAJ (District of Delaware).

Wilson, et al., Chapter 1, "Introduction to the Glucose Sensing Problem," In Vivo Glucose Sensing, 32 pages (2010).

Wisniewski, et al., "Characterization of implantable biosensor membrane biofouling", Fresenius J Anal Chem, 366:611-621 (2000).

Dorland's Illustrated Medical 31$^{st}$ Edition Dictionary, definition of "fluid, interstitial", (2007), 3 pages.

Forlenza, G.P., et al., "Factory-Calibrated Continuous Glucose Monitoring: How and Why It Works, and the Dangers of Reuse Beyond Approved Duration of Wear", Diabetes Technology & Therapeutics, vol. 21, No. 4, (2019) 13 pages.

Stephens Inc., Research Bulletin, "DexCom, Inc., A True Game Changer: The G6 Eliminates Fingersticks", (2018) 5 pages.

The American Heritage® Medical Dictionary, definition of "catheter" and "interstitial fluid", (2007), 4 pages.

OPTIMIZING ANALYTE SENSOR CALIBRATION

RELATED APPLICATIONS

The present application is a continuation of U.S. patent application Ser. No. 17/834,004 filed Jun. 7, 2022, which is a continuation of U.S. patent application Ser. No. 17/556,894 filed Dec. 20, 2021, now U.S. Pat. No. 11,464,434, which is a continuation of U.S. patent application Ser. No. 17/328,768 filed May 24, 2021, now U.S. Pat. No. 11,202,592, which is a continuation of U.S. patent application Ser. No. 17/097,022 filed Nov. 13, 2020, now U.S. Pat. No. 11,013,439, which is a continuation of U.S. patent application Ser. No. 15/604,648 filed May 24, 2017, which is a continuation of U.S. patent application Ser. No. 14/285,575 filed May 22, 2014, now U.S. Pat. No. 9,662,056, which is a continuation of U.S. patent application Ser. No. 13/544,934 filed Jul. 9, 2012, now U.S. Pat. No. 8,744,547, which is a continuation of U.S. patent application Ser. No. 12/242,823 filed Sep. 30, 2008, now U.S. Pat. No. 8,219,173, entitled "Optimizing Analyte Sensor Calibration", the disclosures of each of which are incorporated herein by reference for all purposes.

TECHNICAL FIELD

The present disclosure relates to analyte monitoring devices and systems. More specifically, the present disclosure relates to optimizing calibration of analyte sensors in analyte monitoring devices and systems.

BACKGROUND

There are significant therapeutic advantages for continuously monitoring analyte levels such as glucose levels of diabetic patients. Commercially available continuous glucose monitoring systems use analyte sensors that detect the glucose levels of the patients for a predetermined time period. During this time period, the analyte sensor is generally required to be periodically calibrated with a blood glucose measurement using, for example, an in vitro blood glucose meter.

Calibration of an analyte sensor typically follows a calibration schedule over the life of the analyte sensor, and are intended to maintain the accuracy of the analyte sensor during its useful life. Each calibration routine requires analysis of data from the analyte sensor in conjunction with a reference value, such as from a finger prick test using a lancing device in conjunction with a conventional blood glucose meter. While other areas of the body may be used to perform the blood glucose measurement, such measurement typically requires drawing a blood sample from the patient and applying the blood sample to a blood glucose test strip. This is often a painful experience, which must be performed periodically based on the calibration schedule of the analyte sensor.

SUMMARY

In accordance with the various embodiments of the present disclosure, there are provided method and apparatus for receiving a current blood glucose measurement, retrieving a time information for an upcoming scheduled calibration event for calibrating an analyte sensor, determining temporal proximity between the current blood glucose measurement and the retrieved time information for the upcoming calibration event, and initiating a calibration routine to calibrate the analyte sensor when the determined temporal proximity is within a predetermined time period.

In another aspect, method and apparatus include receiving a current reference data associated with a monitored analyte level, determining whether a next scheduled calibration event for calibrating an analyte sensor associated with the monitored analyte level is within a predetermined time period, validating one or more conditions associated with the calibration of the analyte sensor when the next scheduled calibration event is determined to be within the predetermined time period, and calibrating the analyte sensor based on the received current reference data.

In still a further aspect, an apparatus includes one or more processors; and a memory operatively coupled to the one or more processors for storing instructions which, when executed by the one or more processors, retrieves a time information for an upcoming scheduled calibration event for calibrating an analyte sensor when a current blood glucose measurement is received, determines a temporal proximity between the current blood glucose measurement and the retrieved time information for the upcoming calibration event, and initiates a calibration routine to calibrate the analyte sensor when the determined temporal proximity is within a predetermined time period.

These and other objects, features and advantages of the present disclosure will become more fully apparent from the following detailed description of the embodiments, the appended claims and the accompanying drawings.

DETAILED DESCRIPTION

Figure 1:
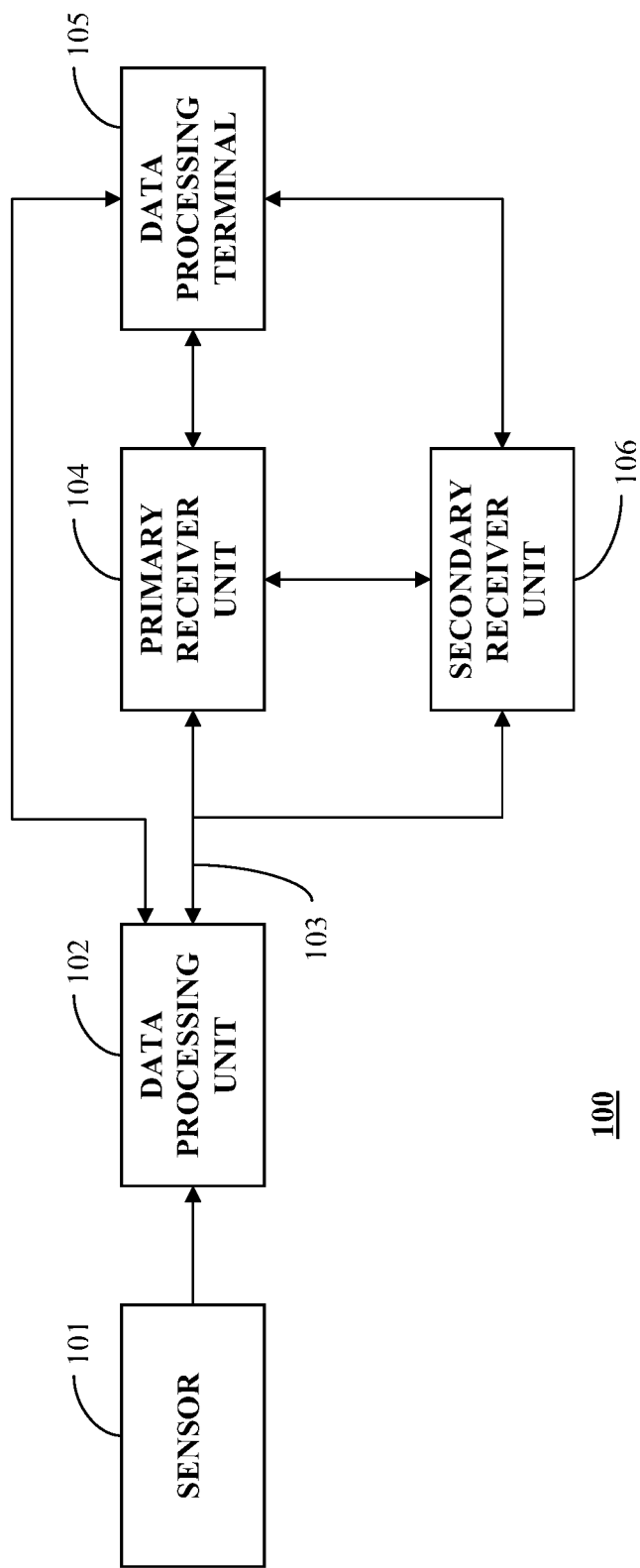
FIG. 1 is a block diagram illustrating an overall system for practicing one or more embodiments of the present disclosure.

Before the present disclosure is described, it is to be understood that this invention is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges as also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and devices for detecting at least one analyte such as glucose in body fluid. In certain embodiments, the present disclosure relates to the continuous and/or automatic in vivo monitoring of the level of an analyte using an analyte sensor.

Accordingly, embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise.

The analyte level may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors of the subject invention may be configured for monitoring the level of the analyte over a time period which may range from minutes, hours, days, weeks, or longer.

Of interest are analyte sensors, such as glucose sensors, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month. Future analyte levels may be predicted based on information obtained, e.g., the current analyte level at time to, the rate of change of the analyte, etc. Predictive alarms may notify the user of predicted analyte levels that may be of concern prior in advance of the analyte level reaching the future level. This enables the user an opportunity to take corrective action.

As described in detail below, in accordance with the various embodiments of the present disclosure, there are provided method, apparatus and system for optimizing analyte sensor calibration to minimize the number of blood glucose measurements in conjunction with the sensor calibration schedule while maintaining the integrity of sensor accuracy.

FIG. 1 shows a data monitoring and management system such as, for example, an analyte (e.g., glucose) monitoring system 100 in accordance with certain embodiments. Embodiments of the subject invention are further described primarily with respect to glucose monitoring devices and systems, and methods of glucose detection, for convenience only and such description is in no way intended to limit the scope of the invention. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 in one embodiment includes a sensor 101, a data processing unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104, the data processing terminal 105 or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or bi-directional communication device.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique identification codes (IDs), communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In one aspect, the primary receiver unit 104 may include an analog interface section including an RF receiver and an antenna that is configured to communicate with the data processing unit 102 via the communication link 103, data processing unit 102 and a data processing section for processing the received data from the data processing unit 102 such as data decoding, error detection and correction, data clock generation, and/or data bit recovery.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring back to FIG. 1, each of the primary receiver unit 104 and the secondary receiver unit 106 may include a blood glucose test strip port such that the user or the patient may perform finger prick tests using blood glucose test strips. Accordingly, in aspects of the present disclosure, the primary receiver unit 104 and the secondary receiver unit 106 may incorporate the functionalities of a blood glucose meter for processing a blood sample to determine a corresponding blood glucose measurement which may be performed by one or more controllers provided in the receiver unit including, for example, a microprocessor, application specific integrated circuit and/or a state machine for executing one or more routines associated with the processing and determination of blood glucose sample to determine the blood glucose level.

Exemplary analyte systems including calibration of analyte sensors that may be employed are described in, for example, U.S. Pat. Nos. 6,134,461, 6,175,752, 6,121,611, 6,560,471, 6,746,582, 7,299,082 and in U.S. patent application Ser. No. 10/745,878 filed Dec. 26, 2003, now U.S. Pat. No. 7,811,231, entitled "Continuous Glucose Monitoring System and Methods of Use", the disclosures of each of which are herein incorporated by reference.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone, Palm® device, Blackberry® device or similar device), mp3 player, pager, and the like), drug delivery device, each of which may be configured for data communication with the receiver via a wired or a wireless connection. Additionally, the data processing terminal 105 may further be connected to a data network (not shown) for additionally storing, retrieving, updating, and/or analyzing data corresponding to the detected analyte level of the user.

In certain embodiments, the communication link 103 as well as one or more of the other communication interfaces shown in FIG. 1 to communicate data between the data processing unit 102, the primary receiver unit 104, secondary receiver unit 106 and the data processing terminal 105 may use one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Furthermore, data communication between the primary receiver unit 104 and the data processing terminal 105, or between the secondary receiver unit 106 and the data processing terminal 105 may include wireless or wired connection such as USB connection, RS-232 connection, serial connection, and the like, to transfer data between the one or more of the primary and the secondary receiver units 104, 106 to the data processing terminal 105.

Figure 2:
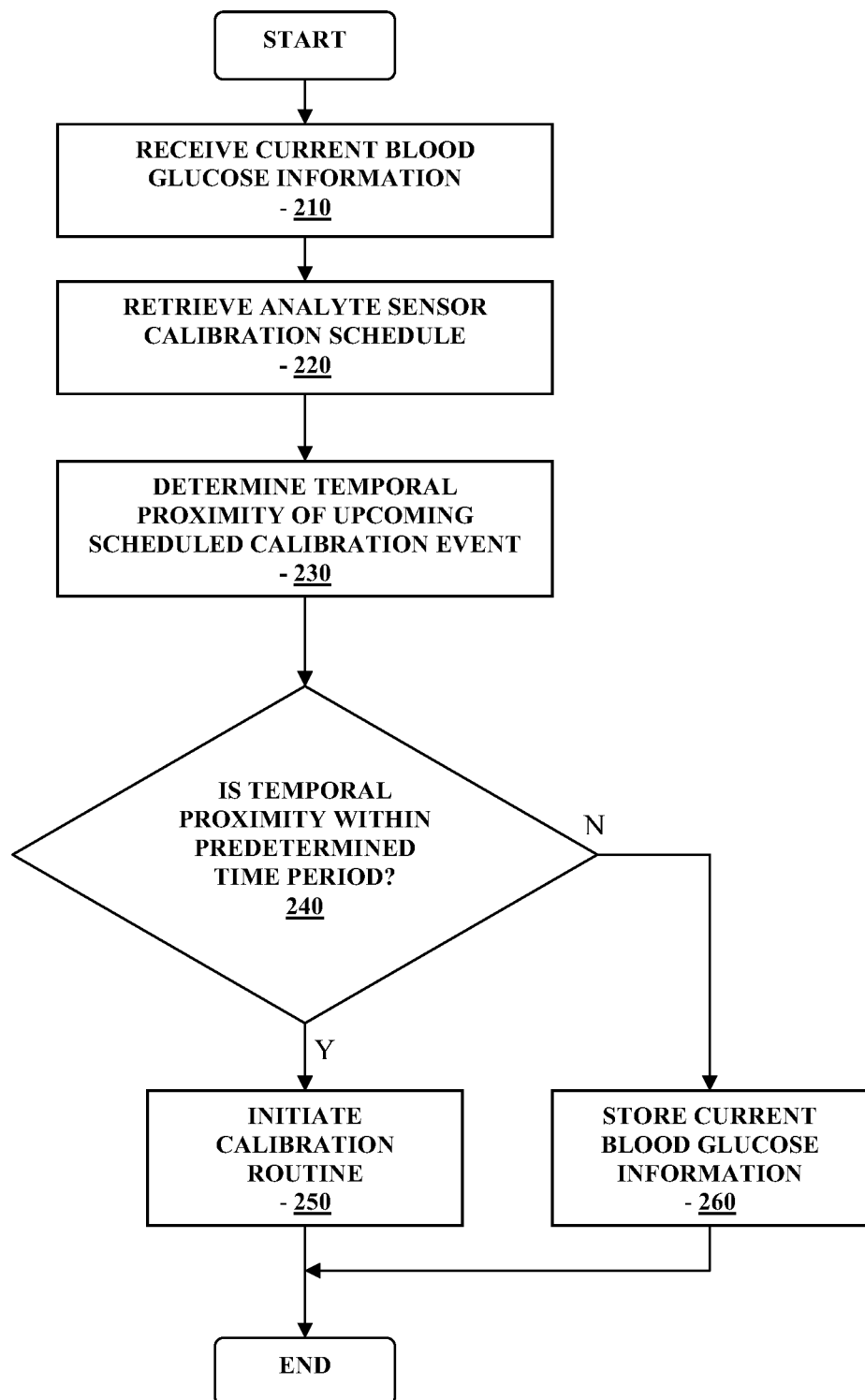
FIG. 2 is an example flowchart for optimizing analyte sensor calibration in accordance with one embodiment of the present disclosure.

FIG. 2 is an example flowchart for optimizing analyte sensor calibration in accordance with one embodiment of the present disclosure. Referring to FIG. 2, in one aspect, when a blood glucose information is received (210) for example, using a finger prick test using a blood glucose test strip, an analyte sensor calibration schedule associated with the analyte sensor 101 (FIG. 1) is retrieved (220). In one aspect, the calibration schedule may include a predetermined time interval at which the sensor 101 is calibrated using a reference measurement such as a blood glucose measurement. In one aspect, one or more memory module or storage unit of the receiver unit 104/106 may store the calibration schedule associated with the sensor 101.

Referring back to FIG. 2, with the retrieved analyte sensor calibration schedule, a temporal proximity of the next upcoming scheduled calibration event is determined (230). That is, in one aspect, when a blood glucose measurement is received, the sensor calibration schedule is reviewed to determine when the next scheduled calibration event is to occur. Thereafter, the temporal proximity is compared to a predetermined time period to determine whether the timing of when the current blood glucose measurement is within a time window associated with the next scheduled calibration event (240).

For example, given an exemplary calibration schedule of 10 hours, 12 hours, 24 hours and 72 hours measured from the analyte sensor positioning in the patient, when the reference blood glucose measurement is received at the $23^{rd}$ hour from when the sensor was positioned in the patient, the temporal proximity is determined to be approximately one hour from the next scheduled calibration event (at the $24^{th}$ hour). The temporal proximity is then compared to the predetermined time period which may be pre-programmed, for example, in the receiver unit (104/106) and may include, for example 90 minutes.

That is, in the example provided above, when a blood glucose measurement is received not in response to an execution of a calibration routine to calibrate the sensor 101, it is determined whether the timing of the received blood glucose measurement is within the predetermined time period from the next scheduled calibration event. Referring back to FIG. 2, if it is determined that the temporal proximity of the upcoming or next scheduled calibration event is within the predetermined time period, then the calibration routine to calibrate the analyte sensor is initiated (250).

In one embodiment, when the calibration routine is initiated, a preliminary check, the calibration conditions are evaluated to determine if calibration of the analyte sensor is appropriate, and when it is determined that the calibration conditions are appropriate, the routine proceeds with executing one or more functions associated with the calibration of the analyte sensor. Moreover, as part of the calibration routine, when initiated, the current blood glucose information as well as other data or information may be stored in a memory or storage unit of the receiver unit 104/106.

Referring back to FIG. 2, on the other hand, if it is determined that the temporal proximity is not within the predetermined time period (240), the current blood glucose measurement received is stored, for example, in a memory or storage unit of the receiver unit 104/106 (260). Additionally, the user or the patient may be notified of the successful calibration event, and further, that the successful calibration event overrides the upcoming scheduled calibration, and that the user or the patient will not be prompted or requested to perform the upcoming scheduled calibration including providing another blood glucose information.

In this manner, in one aspect, when the patient or the user of the analyte monitoring system 100 (FIG. 1) performs a blood glucose measurement between the scheduled calibration time periods, a determination is made to accept the blood glucose measurement to perform calibration of the analyte sensor 101. Thereafter, the upcoming or next scheduled calibration event may be overridden or updated with the calibration performed based on the blood glucose measurement received.

Accordingly, additional flexibility and robustness may be provided in the analyte monitoring system 100 while minimizing the number of blood glucose measurements to calibrate the analyte sensor 101 during its useful life. In other words, when the patient or the user of the analyte monitoring system 100 performs a self-initiated blood glucose measurement (for example, using a standard blood glucose meter, or using the receiver unit 104/106 having such functionality integrated therein), in one aspect, it is determined whether the blood glucose measurement may be used to perform calibration of the analyte sensor, and in which case, the next scheduled calibration event may be overridden or not performed as the conditions are such that the calibration routine using the received current blood glucose measurement may replace the upcoming scheduled calibration event.

By way of an example, there may be circumstances where patient motivated blood glucose measurements are performed sufficiently close to the next scheduled calibration of the analyte sensor 101 such that the next scheduled calibration event may be replaced with the calibration routine performed based on the patient motivated blood glucose measurements. Accordingly, in one aspect, the patient or the user of the analyte monitoring system 100 may be subject to one less finger prick test to determine blood glucose measurement to calibrate the analyte sensor 101.

While particular examples are provided above for the predetermined time period used to compare the temporal proximity of the current blood glucose measurement to the next or upcoming scheduled calibration event, and further, while particular example calibration schedule is described above, within the scope of the present disclosure, the particular predetermined time period to compare the temporal proximity of the blood glucose measurement, or the particular calibration schedule may be varied. For example, the calibration schedule may be provided to require calibration routine once every 24 hours measured from the initial sensor insertion. Alternatively, the calibration schedule time periods may be different for each period during the life of the sensor (which may be 3 days, 5 days, 7 days or more), and further, each subsequent calibration routine after the initial calibration may be determined relative to the immediately preceding successful calibration routine performed, and not relative to the time associated with the initial sensor insertion. Moreover, the predetermined time period used to compare the temporal proximity may include other time periods such as approximately one hour, or approximately two hours, or any other suitable time period rather than approximately 90 minutes.

Figure 3:
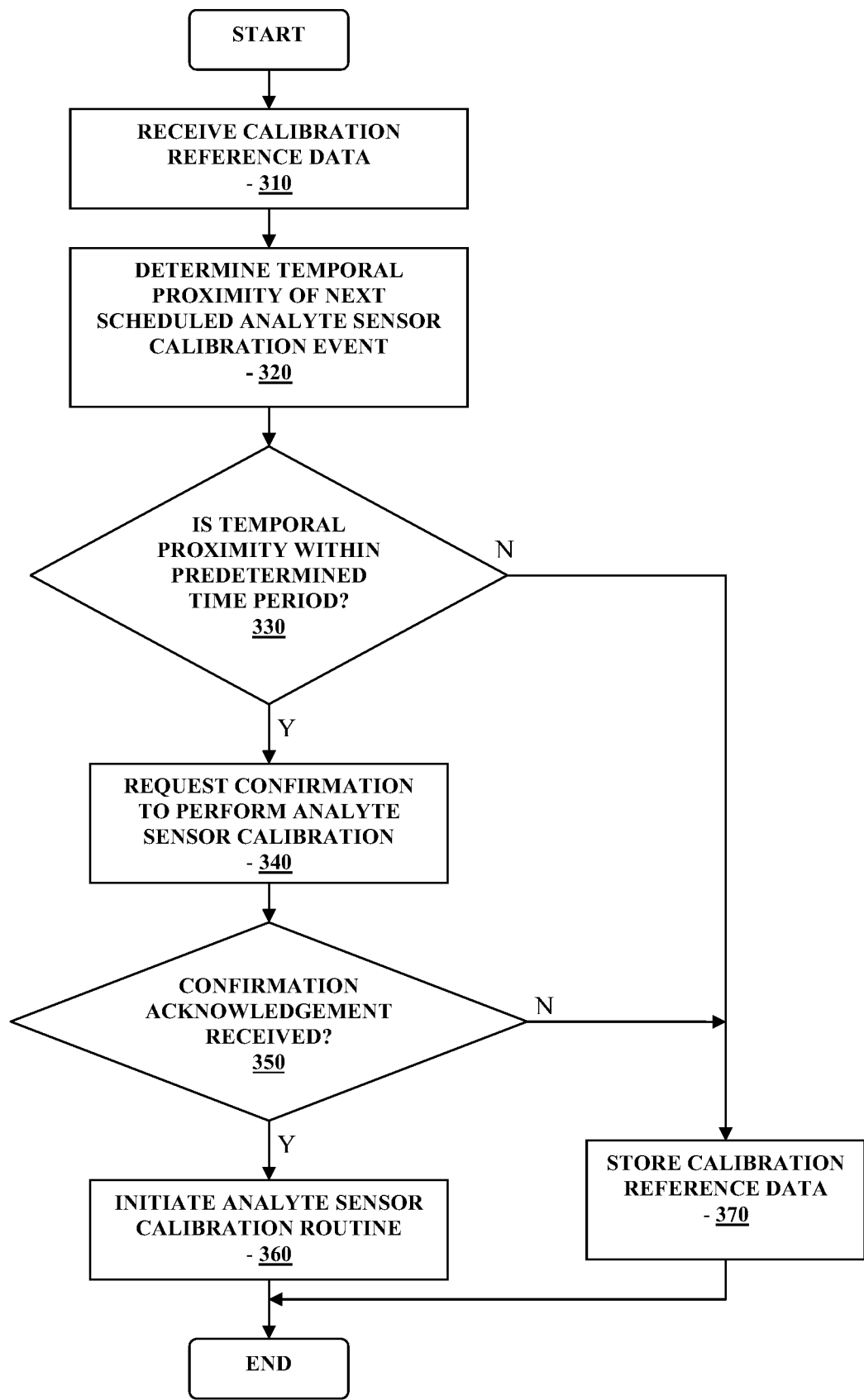
FIG. 3 is an example flowchart for optimizing analyte sensor calibration in accordance with another embodiment of the present disclosure.

FIG. 3 is an example flowchart for optimizing analyte sensor calibration in accordance with another embodiment of the present disclosure. Referring to FIG. 3, in a further aspect, after receiving calibration reference data (310), temporal proximity of the next scheduled analyte sensor calibration event is determined (320). Thereafter, the determined temporal proximity is compared to a predetermined time period as described above (330), and when it is determined that the temporal proximity is not within the predetermined time period, the received calibration reference data is stored (370) and the routine terminates.

On the other hand, referring back to FIG. 3, when it is determined that the temporal proximity of the next scheduled analyte sensor calibration event is within the predetermined time period (relative to when the calibration reference data is received, for example), a request to confirm analyte sensor calibration may be generated and provided to the user or the patient (340). In this manner, the user or the patient may be provided with an opportunity to accept or decline the execution of the calibration routine based on the calibration reference data given the temporal proximity of the next or subsequent upcoming calibration schedule to calibrate the analyte sensor 101 (FIG. 1).

In one aspect, using an output device such as a display on the receiver unit 104/106, the user may be prompted to confirm the execution of the calibration routine in addition to providing information associated with when the next scheduled calibration is to occur. Referring yet again to FIG. 3, when user confirmation acknowledgement is not received (350), then the calibration reference data is stored (370) and the routine terminates. On the other hand, if the user confirmation acknowledgement is received (350), then the analyte sensor calibration routine is initiated (360) to execute the routine associated with the calibration of the analyte sensor. As discussed above, as part of the initiated calibration routine, the calibration reference data as well as other information and data may be stored in the memory or storage device of the receiver unit 104/106.

Referring back to FIG. 3, in a further aspect, when it is determined that the temporal proximity of the next scheduled analyte sensor calibration event is within the predetermined time period, prior to sending the request to confirm the calibration event, calibration conditions may be evaluated to determine whether analyte sensor calibration conditions are appropriate. Alternatively, evaluation of the calibration conditions may be performed after the user or the patient has provided acknowledgement confirmation to perform the calibration.

As discussed in further detail below, initiating the calibration routine may include, in one aspect, validating or confirming the acceptability of the received calibration reference data (for example, a determination that the blood glucose measurement used as the calibration reference data is within a predefined acceptable range such as 40 mg/dL to 400 mg/dL). Additionally, conditions or parameters associated with the execution of the calibration routine may be performed including, for example, determining the rate of the change of the analyte level to be within an acceptable range for calibration, the temperature information associated with the analyte sensor is within an acceptable range, or there are a sufficient number of analyte sensor data points to perform calibration.

Figure 4:
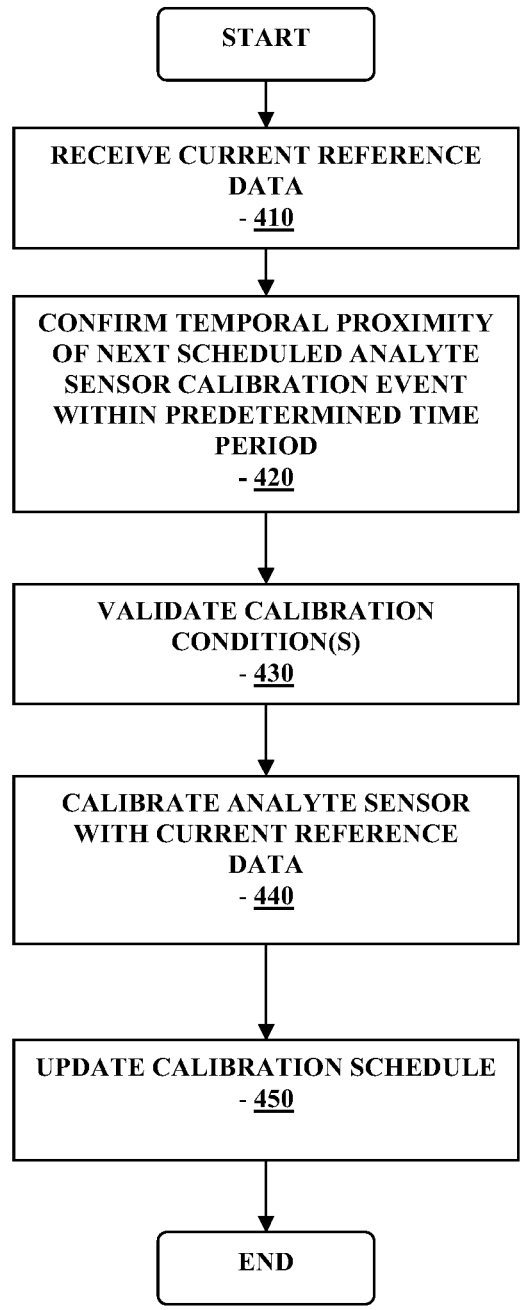
FIG. 4 is an example flowchart for optimizing analyte sensor calibration in accordance with yet another embodiment of the present disclosure.

FIG. 4 is an example flowchart for optimizing analyte sensor calibration in accordance with yet another embodiment of the present disclosure. Referring to FIG. 4, in one aspect, when the current reference data is received (410), temporal proximity of the next scheduled analyte sensor calibration event is confirmed to be within a predetermined time period (for example, such as 90 minutes from when the current reference data is received) (420). Thereafter, calibration conditions are validated to determine that conditions associated with the patient and the analyte sensor, among others, are appropriate (430).

For example, in one aspect, the calibration condition may not be valid when the rate of change of the analyte level exceeds a predetermined threshold level or range. In another aspect, the calibration condition may be determined to be invalid when insufficient analyte sensor data points are present (whether due to data packet drop outs from the data processing unit 102 (FIG. 1), or signal dropout events such as signal attenuation. Within the scope of the present disclosure, other parameters and/or conditions are reviewed and analyzed to determine whether the calibration condition is valid. Examples of such other parameters or conditions are further described in U.S. Pat. Nos. 6,175,752 and 7,299,083, among others, the disclosure of each of which are incorporated by reference for all purposes.

Referring back to FIG. 4, upon validation of the calibration conditions (430), the analyte sensor is calibrated using the received current reference data (440). Moreover, after calibration, the stored calibration schedule in one aspect may be retrieved and updated to include the calibration performed based on the received current reference data (450). Moreover, in one aspect, the retrieved calibration schedule may be updated to replace the next scheduled analyte sensor calibration event with the calibration based on the current reference data.

In the manner provided, within the scope of the present disclosure, using the non-calibration prompted and user initiated blood glucose measurements, under certain conditions such as time proximity to the subsequent scheduled calibration event, among others, the number of required blood glucose measurement using a blood glucose test strip may be minimized.

Referring still to the various embodiments of the present disclosure, as discussed above, the analyte monitoring system may automatically perform the calibration of the analyte sensor based on the blood glucose measurement received, and thereafter, notify the user or the patient of the successful calibration of the sensor, or alternatively, provide the patient or the user with the option to confirm the performance of the calibration of the sensor based on the receive blood glucose measurement. Within the scope of the present disclosure, other variations or levels of user or patient interaction may be contemplated, such as, for example, notification (alarms or alerts that are visual, auditory, vibratory or one or more combinations thereof) to the user of calibration associated events such as updating the previously stored calibration schedule based on the calibration performed with the current reference or blood glucose data, notification of the next valid scheduled calibration, the number of calibrations remaining for the sensor prior to sensor replacement, failed calibration attempt, unsuitable calibration conditions, verified valid calibration conditions, and the like.

Accordingly, a method in one aspect includes receiving a current blood glucose measurement, retrieving a time information for an upcoming scheduled calibration event for calibrating an analyte sensor, determining temporal proximity between the current blood glucose measurement and the retrieved time information for the upcoming calibration event, and initiating a calibration routine to calibrate the analyte sensor when the determined temporal proximity is within a predetermined time period.

In one aspect, initiating the calibration routine may include calibrating the analyte sensor based on the received current blood glucose measurement.

Moreover, the method may include determining validity of the current blood glucose measurement, for example, by comparing the current blood glucose measurement to predetermined ranges or values.

Additionally, determining validity of the current blood glucose measurement may include analyzing the current blood glucose measurement based on a predetermined threshold range, a temperature information, or a combination thereof.

In still another aspect, the method may include determining the validity of an analyte sensor data, including one or more of analyzing the analyte sensor data based on one or more of a rate of change of the analyte level, a temperature information, a predetermined analyte level threshold range, or one or more combinations thereof.

In another aspect, the method may include overriding the upcoming scheduled calibration event when the calibration routine to calibrate the analyte sensor based on the received current blood glucose measurement is successful.

Also, initiating the calibration routine may include validating one or more calibration condition parameters associated with the calibration of the analyte sensor.

Yet still further aspect may include generating an output signal confirming completion of the upcoming scheduled calibration event.

In yet another aspect, the method may include updating a calibration schedule for calibrating the analyte sensor based on the initiated calibration routine.

Further, initiating calibration routine may include automatically performing the calibration routine to calibrate the analyte sensor when the determined temporal proximity is within the predetermined time period.

A method in accordance with another aspect of the present disclosure includes receiving a current reference data associated with a monitored analyte level, determining whether a next scheduled calibration event for calibrating an analyte sensor associated with the monitored analyte level is within a predetermined time period, validating one or more conditions associated with the calibration of the analyte sensor when the next scheduled calibration event is determined to be within the predetermined time period, and calibrating the analyte sensor based on the received current reference data.

The analyte sensor may be associated with a time spaced calibration schedule including the next scheduled calibration event.

The time spaced calibration schedule may include an unevenly time spaced calibration schedule during the life of the sensor.

In another aspect, the method may include updating the time spaced calibration schedule based on analyte sensor calibration using the received current reference data Also, the method may include associating the current reference data with a corresponding calibrated analyte sensor data.

Additionally, in a further aspect, the method may include disabling a calibration routine associated with the next scheduled calibration event.

An apparatus in accordance with another aspect of the present disclosure includes one or more processors, and a memory operatively coupled to the one or more processors for storing instructions which, when executed by the one or more processors, retrieves a time information for an upcoming scheduled calibration event for calibrating an analyte sensor when a current blood glucose measurement is received, determines a temporal proximity between the current blood glucose measurement and the retrieved time information for the upcoming calibration event, and initiates a calibration routine to calibrate the analyte sensor when the determined temporal proximity is within a predetermined time period.

The apparatus may include a blood glucose strip port configured to receive a blood glucose test strip providing the current blood glucose measurement. That is, in one aspect, the receiver unit 104/106 (FIG. 1) may include an integrated blood glucose test strip port and be configured to analyze the blood sample received from the test strip to determine the corresponding blood glucose level.

In still another aspect, the apparatus may include a housing coupled to the blood glucose strip port and further, wherein the one or more processors and the memory are provided in the housing.

The various processes described above including the processes performed by the one or more processors of the receiver unit 104/106, or optionally the data processing unit 102 (FIG. 1), in the software application execution environment as well as any other suitable or similar processing units embodied in the analyte monitoring system 100, including the processes and routines described in conjunction with FIGS. 2-4, may be embodied as computer programs developed using an object oriented language that allows the modeling of complex systems with modular objects to create abstractions that are representative of real world, physical objects and their interrelationships. The software required to carry out the inventive process, which may be stored in a memory (or similar storage devices in the data processing unit 102, or the receiver unit 104/106) of the processor, may be developed by a person of ordinary skill in the art and may include one or more computer program products.

Various other modifications and alterations in the structure and method of operation of this present disclosure will be apparent to those skilled in the art without departing from the scope and spirit of the present disclosure. Although the present disclosure has been described in connection with specific preferred embodiments, it should be understood that the present disclosure as claimed should not be unduly limited to such specific embodiments. It is intended that the following claims define the scope of the present disclosure and that structures and methods within the scope of these claims and their equivalents be covered thereby.

What is claimed is:

1. A continuous glucose monitoring system, comprising:
   a glucose sensor having a first portion configured to be positioned through a user's skin and in contact with an interstitial fluid of the user for in vivo detection of glucose and a second portion configured to remain above the user's skin;
   a non-transitory memory; and
   at least one processor communicatively coupled to the non-transitory memory and the glucose sensor and configured to:
      receive a current blood glucose measurement of the user determined based on a finger prick test using a lancing device in conjunction with a blood glucose meter;
      provide a prompt to accept or decline execution of a calibration routine using the current blood glucose measurement;
      upon receiving an acceptance to the prompt to accept or decline execution of a calibration routine using the current blood glucose measurement, confirm:
         (1) that the current blood glucose measurement is within a glucose-value range, and
         (2) that a rate of change of a glucose level detected by the glucose sensor is within a rate-of-change range;
      upon confirming (1) and (2) initiate the calibration routine and calibrate the glucose sensor using the current blood glucose measurement;
      wherein if a declination to the prompt to accept or decline execution of a calibration routine using the current blood glucose measurement is received, the at least one processor is further configured to store the current blood glucose measurement.

2. The system of claim 1, wherein the glucose-value range is between 40 mg/dL and 400 mg/dL.

3. The system of claim 1, wherein upon receiving the acceptance to the prompt to accept or decline execution of the calibration routine using the current blood glucose measurement, the processor is further configured to confirm a number of analyte sensor data points to initiate the calibration routine is above a threshold.

4. The system of claim 1, wherein upon receiving the acceptance to the prompt to accept or decline execution of the calibration routine using the current blood glucose measurement, the processor is further configured to confirm that a temperature associated with the glucose monitoring system is within a temperature range.

5. The system of claim 1, wherein the calibration routine comprises storing the current blood glucose measurement.

6. The system of claim 1, wherein the processor is further configured to determine if the calibration routine failed.

7. The system of claim 6, wherein the processor is further configured to provide a notification if the calibration routine failed.

8. The system of claim 1, wherein the processor is further configured to store a calibration schedule in the non-transitory memory, wherein the calibration schedule comprises a plurality of scheduled calibration events for receiving scheduled blood glucose measurements to calibrate the glucose sensor.

9. The system of claim 8, wherein the processor is further configured to determine if the current blood glucose measurement is within a predetermined time period from an upcoming scheduled calibration event.

10. The system of claim 9, wherein the processor is further configured to update the calibration schedule to replace the upcoming scheduled calibration event with the calibration routine.

11. The system of claim 9, wherein the predetermined time period is 90 minutes.

12. A method comprising:
receiving, by at least one processor, a current blood glucose measurement of the user determined based on a finger prick test using a lancing device in conjunction with a blood glucose meter;
providing, by the at least one processor, a prompt to accept or decline execution of a calibration routine using the current blood glucose measurement;
upon receiving an acceptance to the prompt to accept or decline execution of a calibration routine using the current blood glucose measurement, confirming, by the at least one processor:
(1) that the current blood glucose measurement is within a glucose-value range, and
(2) that a rate of change of a glucose level detected by a glucose sensor is within a rate-of-change range;
upon confirming (1) and (2), initiating, by the at least one processor the calibration routine and calibrate the glucose sensor using the current blood glucose measurement;
wherein if a declination to the prompt to accept or decline execution of a calibration routine using the current blood glucose measurement is received, storing, by the at least one processor, the current blood glucose measurement.

13. The method of claim 12, wherein the glucose-value range is between 40 mg/dL and 400 mg/dL.

14. The method of claim 12, wherein upon receiving the acceptance to the prompt to accept or decline execution of the calibration routine using the current blood glucose measurement, the method further comprises confirming, by the at least one processor, a number of analyte sensor data points to initiate the calibration routine is above a threshold.

15. The method of claim 12, wherein upon receiving the acceptance to the prompt to accept or decline execution of the calibration routine using the current blood glucose measurement, the method further comprises confirming, by the at least one processor, that a temperature associated with the glucose monitoring system is within a temperature range.

16. The method of claim 12, wherein the calibration routine comprises storing the current blood glucose measurement.

17. The method of claim 12, wherein the method further comprises determining, by the at least one processor, if the calibration routine failed.

18. The method of claim 17, wherein the method further comprises providing, by the at least one processor, a notification if the calibration routine failed.

19. The method of claim 12, wherein the method further comprises storing, by the at least one processor, a calibration schedule in the non-transitory memory, wherein the calibration schedule comprises a plurality of scheduled calibration events for receiving scheduled blood glucose measurements to calibrate the glucose sensor.

20. The method of claim 19, wherein the method further comprises determining, by the at least one processor, if the current blood glucose measurement is within a predetermined time period from an upcoming scheduled calibration event.

21. The method of claim 20, wherein the method further comprises updating, by the at least one processor, the calibration schedule to replace the upcoming scheduled calibration event with the calibration routine.

22. The method of claim 20, wherein the predetermined time period is 90 minutes.

* * * * *